US007513159B2

(12) United States Patent
Komeyama et al.

(10) Patent No.: US 7,513,159 B2
(45) Date of Patent: Apr. 7, 2009

(54) SHAFT COUPLING MONITORING APPARATUS

(75) Inventors: Nobuo Komeyama, Nara (JP); Kenji Sakamoto, Nara (JP)

(73) Assignee: JTEKT Corporation, Osaka-shi (JP)

( * ) Notice: Subject to any disclaimer, the term of this patent is extended or adjusted under 35 U.S.C. 154(b) by 159 days.

(21) Appl. No.: 11/579,954

(22) PCT Filed: May 16, 2005

(86) PCT No.: PCT/JP2005/008888

§ 371 (c)(1),
(2), (4) Date: Nov. 9, 2006

(87) PCT Pub. No.: WO2005/111451

PCT Pub. Date: Nov. 24, 2005

(65) Prior Publication Data

US 2008/0139325 A1    Jun. 12, 2008

(30) Foreign Application Priority Data

May 17, 2004  (JP) ............................. 2004-146788
May 17, 2004  (JP) ............................. 2004-146836

(51) Int. Cl.
G01M 13/00    (2006.01)
G01H 1/00     (2006.01)
(52) U.S. Cl. .......................................... 73/593; 73/622
(58) Field of Classification Search ................. 73/593, 73/622, 625, 592, 635–640
See application file for complete search history.

(56) References Cited

U.S. PATENT DOCUMENTS 4,331,034 A * 5/1982 Takeda et al. ................. 73/637
4,495,587 A * 1/1985 Plante et al. .................. 702/38
4,798,299 A   1/1989 Bayer et al.
5,600,240 A   2/1997 Mikhailovich et al.
5,971,619 A  10/1999 Bourgeois-Jacquet et al.
2001/0033234 A1 10/2001 Kyrtsos et al.

FOREIGN PATENT DOCUMENTS

| JP | 58-077915 | * | 5/1983 |
| JP | 58-77915 A | | 5/1983 |
| JP | 62-155324 A | | 7/1987 |
| JP | 7-4934 U | | 1/1995 |
| JP | 10-267898 A | | 10/1998 |
| JP | 11-51073 A | | 2/1999 |
| JP | 2001-304975 A | | 10/2001 |

OTHER PUBLICATIONS

CD-ROM of the specification and drawings annexed to the request of Japanese Utility Model Application No. 39701/1993 (Laid-open No. 4934/1995) Koyo Seiko Co., Ltd.), Jan. 24, 1995.

* cited by examiner

*Primary Examiner*—Helen C. Kwok
(74) *Attorney, Agent, or Firm*—Birch, Stewart, Kolasch & Birch, LLP

(57) ABSTRACT

In a shaft coupling monitoring apparatus for monitoring a spider joint using outer peripheries of four shafts of a cross shaft as rolling contact surfaces, each of the shafts contains therein a sensor for detecting any damage on the rolling contact surface thereof. Even in a case where the spider joint is incorporated in a driving shaft such as of a rolling mill, the monitoring apparatus may provide high-accuracy and early detection of any damage such as flaking on the rolling contact surface defined on each of the shafts of the cross shaft.

15 Claims, 15 Drawing Sheets

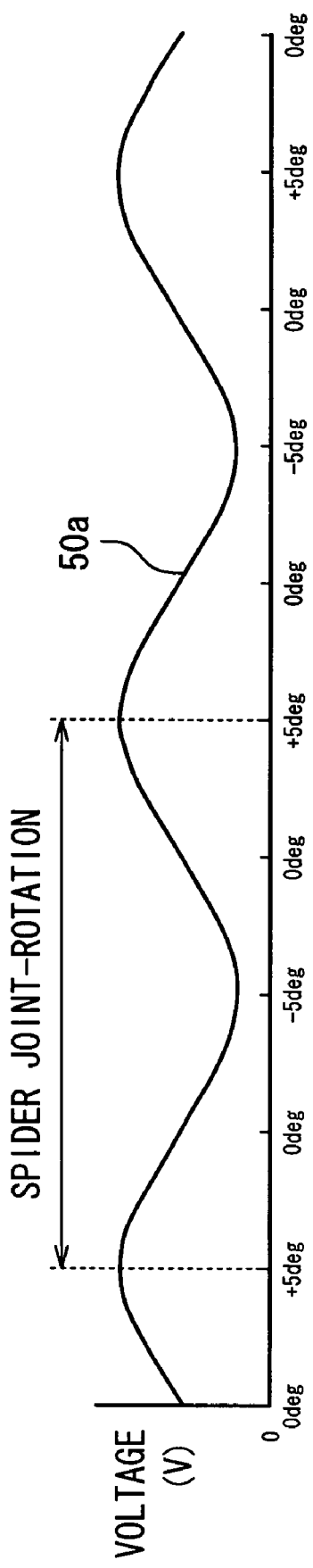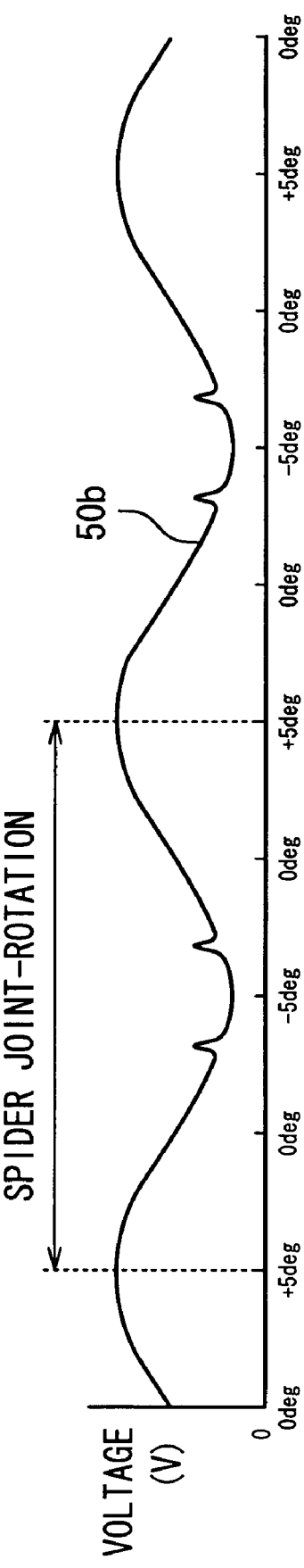

SHAFT COUPLING MONITORING APPARATUS

TECHNICAL FIELD

The present invention relates to a shaft coupling monitoring apparatus for monitoring a spider joint incorporated in a driving shaft such as of a rolling mill.

BACKGROUND ART

In a steel rolling mill, for example, a spider joint is disposed at some place of a driving shaft connected between a mill roll and a drive motor in order to carry out a rolling process as allowing the mill roll to vertically move relative to a steel material being rolled.

The above spider joint includes one which has the following constitution as disclosed in Japanese Unexamined Patent Publication No. H11(1999)-51073, for example. The spider joint is constituted such that a bearing cup is provided on each of four shafts of a cross shaft and rollers are rollably interposed between the cup and the shaft so as to utilize an outer periphery of the shaft as a rolling contact surface. This spider joint has the respective pairs of bearing cups on different lines connected to respective ends of a driving shaft portion and a driven shaft portion respectively disposed on a drive-motor-side and a mill-roll side of the driving shaft, whereby the joint is incorporated in the driving shaft for transmitting a torque of the drive motor to the mill roll side.

By the way, the aforementioned spider joint tends to suffer flaking on a shaft surface according to the length of operation time because the mill roll applies quite a great load to the shafts and bearing cups during the steel rolling process. What is more, the vertical motion of the mill roll causes the bearing cups to pivotally move relative to the shafts on which the bearing cups are mounted. Hence, the rolling contact surface provided on each of the shafts is susceptible to a partial damage such as flaking or cracks, which is produced in a circumferential direction thereof. In cases, the four shafts may suffer different degrees of flaking on a shaft surface.

In the rolling mill or the like, the cross shaft of the spider joint has an axially peripheral portion covered by the four bearing cups, and also has a central portion thereof substantially closely connected with the respective ends of the driving shaft portion and the driven shaft portion. Thus, the spider joint with the cross shaft substantially unexposed to outside is incorporated in the driving shaft. This makes it difficult for the spider joint to be mounted with a sensor for detecting the damage, such as flaking, on the rolling contact surface provided on each of the shafts. Hence, the detection of the damage based on the results of sensor detection is also impracticable. It is therefore required to subject the rolling mill to a periodical inspection, wherein the spider joint is disassembled from the driving shaft and is totally disassembled by dismounting the bearing cups from the shafts, so that the individual shafts may be visually inspected for flaking. This periodical inspection operation takes an enormous quantity of labor and time. In another method, an iron content of spent grease is determined so as to analogize the occurrence of damage on the rolling contact surface of the shaft. The grease is supplied to the rolling contact surface. In this method, however, the detection of damage may not be carried out at any one given point in time. In addition, the detection of damage based on the analogy has poor accuracies. What is more, this method is not adapted for the detection of damage on a per-shaft basis.

It is therefore an object of the invention to provide novel technical means for providing a high-accuracy and early detection of damage, such as flaking on the rolling contact surface provided on the respective shafts of the cross shaft of the spider joint incorporated in the driving shaft of the rolling mill or the like, on a per-shaft basis.

SUMMARY OF THE INVENTION

According to the invention for achieving the above object, a shaft coupling monitoring apparatus for monitoring a spider joint using outer peripheries of four shafts of a cross shaft as rolling contact surfaces for rolling motion of rolling elements is characterized in that the shaft contains therein a sensor for detecting any damage on the rolling contact surface thereof.

According to the shaft coupling monitoring apparatus constituted as described above, the shaft of the cross shaft contains therein the sensor for detecting the damage on the rolling contact surface thereof. Therefore, even in a case where the spider joint with the cross shaft substantially unexposed to outside is incorporated in the driving shaft such as of the rolling mill, the apparatus can accomplish the high-accuracy detection of the damage on the rolling contact surface on a per-shaft basis.

The above shaft coupling monitoring apparatus may also be constituted such that a bearing cup is pivotally mounted on each of the four shafts, and that a displacement sensor for detecting a relative displacement between the shaft and the bearing cup is used as said sensor and disposed at the bearing cup.

The present inventors have found that the shaft coupling monitoring apparatus having the above constitution is adapted to determine whether or not the rolling contact surface sustains the damage such as flaking by detecting the relative displacement between the shaft of the cross shaft and the bearing cup by means of the displacement sensor. Only when the rolling contact surface sustains the damage, the shaft may be deflected due to the damage. An output variation attributable to the deflection of the shaft was observed in the output from the displacement sensor. The invention has been accomplished based on this finding, and is adapted to immediately detect the occurrence of some damage on the rolling contact surface by detecting a variation of the output from the displacement sensor. It is also possible to determine a damaged point or the degree of the damage because the output from the sensor varies according to the damaged point on the rolling contact surface or the degree of the damage. Since the displacement sensor is disposed at the bearing cup, the following advantage may be offered. Even in the case where the spider joint with the cross shaft substantially unexposed to outside is incorporated in the driving shaft such as of the rolling mill, the monitoring apparatus is capable of carrying out the high-accuracy detection of damage on the rolling contact surface on a per-shaft basis, as allowing the sensor along with the bearing cup to be pivotally moved relative to the corresponding shaft. The displacement sensor may be disposed at each of the four shafts of the cross shaft or only at any shaft susceptible to the damage.

It is preferred in the above shaft coupling monitoring apparatus that the displacement sensor is disposed on a line extended in parallel to a rotational direction of the spider joint and passing through the center of the shaft.

In this case, the displacement sensor is disposed at place in a deflection direction of the shaft deflected due to the damage on the rolling contact surface or in a direction 180 deg. opposite of the deflection direction with respect to the shaft center. Thus, the displacement sensor is capable of detecting the deflection-induced displacement/variation with the highest sensitivity, thus accomplishing the detection of damage with higher accuracies.

It is preferred in the above shaft coupling monitoring apparatus that the displacement sensor is disposed in a hole which is formed in the shaft in coaxial relation therewith, and detects the displacement by detecting a distance from an inside wall of this hole.

In this case, the displacement sensor serves to detect the displacement of the shaft as disposed in the shaft itself, which is deflected due to the damage produced on the rolling contact surface thereof. Hence, the sensor may be improved in detection accuracies.

The above shaft coupling monitoring apparatus is characterized in that an ultrasonic sensor capable of outputting an ultrasonic wave toward the rolling contact surface and receiving the ultrasonic wave reflected from the rolling contact surface is used as said sensor and disposed in the shaft.

The present inventors have found that the shaft coupling monitoring apparatus having the above constitution is adapted to determine whether or not the rolling contact surface sustains the damage such as flaking by operating the ultrasonic sensor to output the ultrasonic wave toward the rolling contact surface and to receive the ultrasonic wave reflected from the rolling contact surface. Specifically, in a case where the rolling contact surface is free from damage, the ultrasonic reflective wave from the rolling contact surface is received by the sensor, as hardly attenuated as compared with the ultrasonic outgoing wave. In a case where the rolling contact surface sustains some damage, on the other hand, the ultrasonic wave is diffused by the damage, so that the reflective wave reflected back to the sensor is seriously attenuated or that the sensor may not receive the reflective wave at all. The invention has been accomplished based on this finding and is adapted to immediately detect the occurrence of any damage on the rolling contact surface by detecting a variation of the ultrasonic reflective wave from the rolling contact surface. Since the ultrasonic sensor is disposed in the shaft, the following advantage may be offered. Even in the case where the spider joint with the cross shaft substantially unexposed to outside is incorporated in the driving shaft such as of the rolling mill, the monitoring apparatus is capable of carrying out the high-accuracy detection of damage on the rolling contact surface on a per-shaft basis. The ultrasonic sensor may be disposed at each of the four shafts of the cross shaft or only at any shaft susceptible to the damage.

It is preferred in the above shaft coupling monitoring apparatus that the ultrasonic sensor outputs the ultrasonic outgoing wave toward the rolling contact surface as keeping the outgoing wave in phase with the ultrasonic reflective wave reflected from the rolling contact surface free from damage in order to receive an amplified ultrasonic wave reflected from the rolling contact surface.

In this case, the ultrasonic wave inputted to the ultrasonic sensor as reflected from the rolling contact surface may be increased in the amplitude by interference between the outgoing wave and the reflective wave. Thus, the sensor may achieve an increased accuracy of the detection of damage on the rolling contact surface.

It is preferred in the above shaft coupling monitoring apparatus that a bearing cup is pivotally mounted on each of the four shafts, and that the ultrasonic sensor is disposed in a mounting space provided in the shaft, as fixed to the bearing cup.

In this case, the ultrasonic sensor is fixed to the bearing cup. Therefore, when the bearing cup is pivotally moved relative to the corresponding shaft, the sensor is also pivotally moved in tandem, so that a target point (sensing point) of the ultrasonic outgoing wave on the rolling contact surface may be moved. That is, the ultrasonic sensor is adapted for sequential sensing of the rolling contact surface in accordance with the pivotal motion of the cup. Thus, the ultrasonic sensor is not only capable of applying the ultrasonic wave to a required range without widening the output range of the ultrasonic wave, but also capable of locating the damaged point on the rolling contact surface.

The above shaft coupling monitoring apparatus may also have a constitution wherein the ultrasonic sensor outputs the ultrasonic wave toward the rolling contact surface, as held in close contact against a wall of the mounting space.

This constitution obviates the formation of an interface on an ultrasonic propagation path between the ultrasonic sensor and the rolling contact surface. Thus, the ultrasonic propagation path may be prevented from being changed as refracted by the interface, so that the sensor can provide an exact ultrasonic sensing in respect of a desired point on the rolling contact surface.

In the above shaft coupling monitoring apparatus, the ultrasonic sensor may be disposed in a hole formed as a grease passage in the shaft.

In this case, the ultrasonic sensor may be disposed in the shaft without forming, in the shaft, a hole or recess for mounting the sensor.

BRIEF DESCRIPTION OF THE DRAWINGS

FIG. 6(a) and FIG. 6(b) are waveform charts showing a specific waveform of an output from the above displacement sensor when the rolling contact surface does not sustain any damage and a specific waveform of an output from the sensor when the rolling contact surface sustains some damage;

BEST MODES FOR CARRYING OUT THE INVENTION

A shaft coupling monitoring apparatus according to a preferred embodiment of the invention will hereinbelow be described with reference to the accompanying drawings. The following description is made by way of example of a case where the invention is applied to a spider joint incorporated in a driving shaft of a rolling mill.

Embodiment 1

Figure 1:
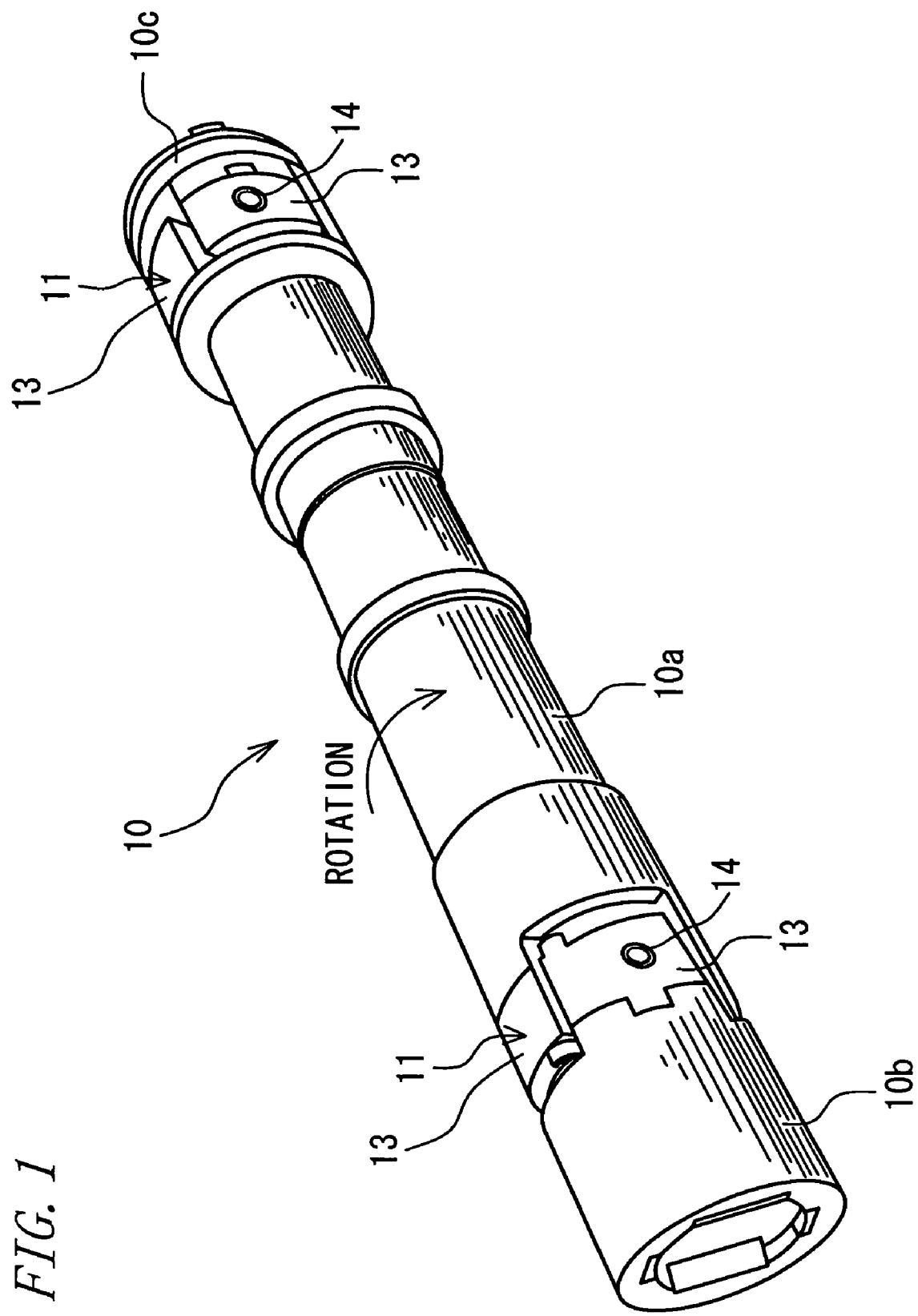
FIG. 1 is a perspective view showing a driving shaft for use in rolling mill of steel manufacturers.
Figure 2:
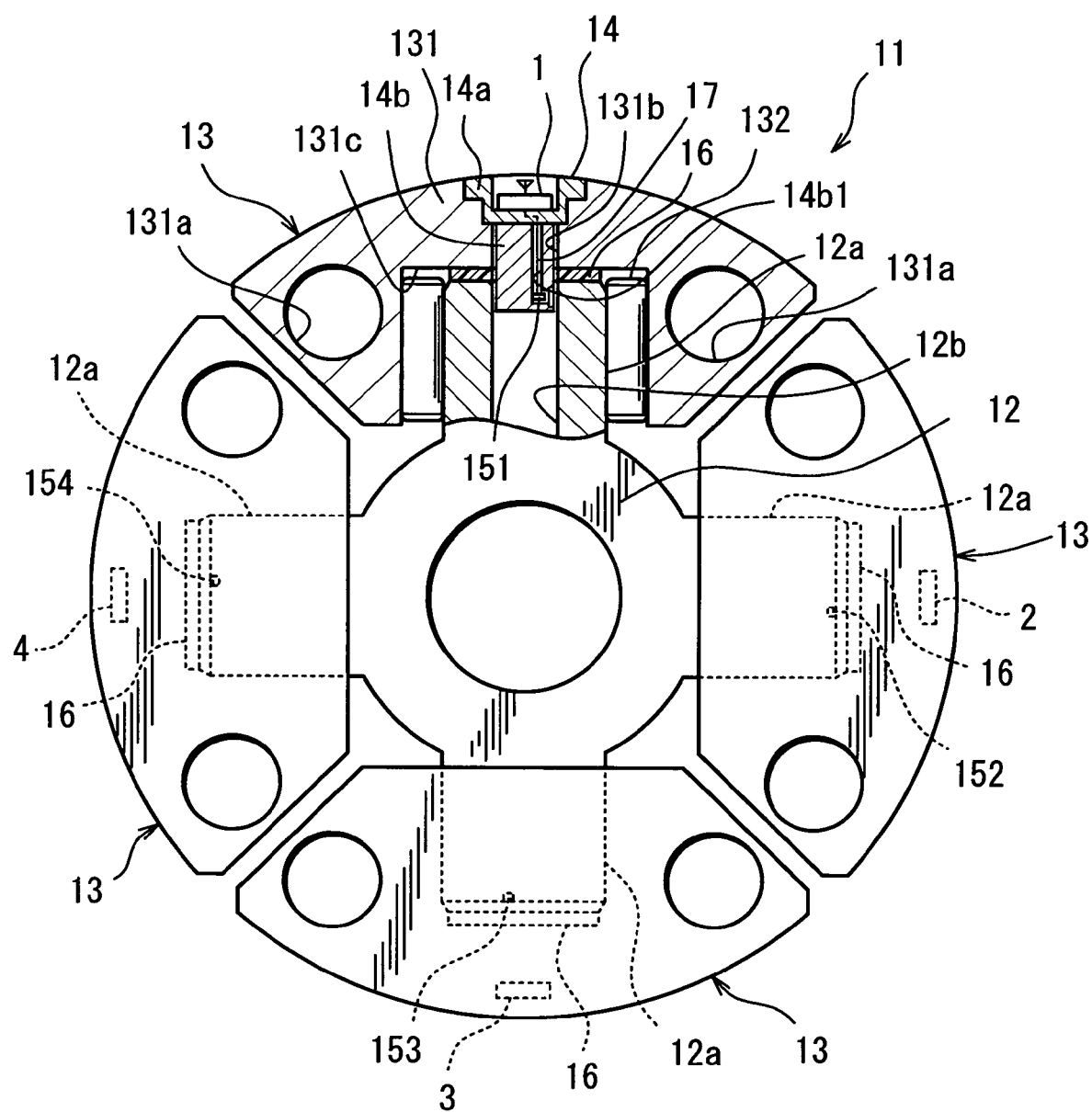
FIG. 2 is a diagram (including a partial sectional view) showing an essential part of a shaft coupling monitoring apparatus according to one embodiment of the invention as viewed in an axial direction of the driving shaft.

FIG. 1 is a perspective view showing a driving shaft for use in the rolling mill of steel manufacturers. FIG. 2 is a diagram (including a partial sectional view) showing an essential part of a shaft coupling monitoring apparatus according to one embodiment of the invention as viewed in an axial direction of the driving shaft. Referring to the figure, a driving shaft 10 has spider joints 11 mounted to places near the opposite ends thereof. The driving shaft 10 has one end and the other end thereof connected with an unillustrated drive motor and an unillustrated mill roll for steel rolling via the respective spider joints 11. Specifically, the driving shaft 10 includes an intermediate shaft portion (a first shaft portion) 10a interposed between the two spider joints 11, as well as a driving shaft portion (a second shaft portion) 10b and a driven shaft portion (a third shaft portion) 10c which are connected with the motor and the roll, respectively. One of the spider joints 11 interconnects the intermediate shaft portion 10a and the driving shaft portion 10b, whereas the other spider joint 11 interconnects the intermediate shaft portion 10a and the driven shaft portion 10c (FIG. 1). The rolling mill has an arrangement wherein two driving shafts 10 are extended in parallel to each other and wherein slab or the like is rolled through the two mill rolls connected with the respective driving shafts 10, thereby forming a rolled steel material. In the rolling process, each of the spider joints 11 transmits a torque of the above drive motor to the milling roll as allowing the connected driving shaft 10 to incline axially. Furthermore, the provision of the spider joints 11 offers an easy adjustment of a distance between axes of the upper and lower milling rolls when the milling roll is worn out or when a roll width of a steel material is changed.

The above spider joint 11 includes a cross shaft 12, and four bearing cups 13. The bearing cups 13 are pivotally mounted to four shafts 12a of the cross shaft 12, respectively, thus covering an axially peripheral portion of the cross shaft 12. Each of the bearing cups 13 includes a closed-end cup portion 131 and a plurality of rollers 132 retained in the cup portion and rollably contacting the above shaft 12a. An outer raceway and an inner raceway are defined by an inner periphery of the cup portion 131 and by an outer periphery of the shaft 12a. A vertical pair of bearing cups 13 as seen in FIG. 2 are connected with the shaft portion of the driving shaft 10 (the a fore said driving shaft portion 10b, for example) on one axial side with respect to the spider joint 11, whereas a transverse pair of bearing cups 13 are connected with the shaft portion of the driving shaft (the aforesaid intermediate shaft portion 10a, for example) on the other axial side with respect to the spider joint 11. Specifically, a cup portion 131 is connected with a flange formed at an end of a corresponding shaft portion of the driving shaft 10 by means of bolts threadedly engaged with bolt holes 131a formed at transversely opposite ends of the cup portion 131. The cross shaft 12 has the right-side and left-side central portions thereof connected substantially in close contact with the respective end of the shaft portions. Thus, the individual shaft portions are connected with the cross shaft 12 barely exposed to outside and incorporated in the driving shaft 10.

The cup portion 131 is formed with a grease injection hole 131b at a circumferentially central portion thereof. A thrust washer 16 such as formed from a synthetic resin material is interposed between a bottom surface 131c of the cup portion 131 and an end of the shaft 12a. Thus, the bearing cup supports the shaft 12a as preventing metal contact between the bottom surface 131c thereof and the end of the shaft. Each of the shafts 12a of the cross shaft 12 is formed with a hole 12b which is in coaxial relation with the aforesaid hole 131b and is concentric about the axis of the shaft 12a. The individual holes 12b of the shafts 12a are intercommunicated within the spider joint 11. The hole 12b constitutes a grease passage through which a grease flows for lubricating a rolling contact portion between an axially outer periphery of the aforesaid roller 132 and an inner periphery of the cup portion.

The above hole 131b has a lid 14 removably mounted thereto, such as to prevent the leakage of the grease flowing from the above rolling contact portion to the outside via the hole 131b. More specifically, the lid 14 includes: a mounting portion 14a shaped like a flat-bottomed cup and tightly contacting a step-like inner periphery, for example, of the hole 131b for substantially sealing the hole 131b; and a rod-like support portion 14b extended from a bottom of the mounting portion in an axial direction of the shaft 12a so as to be inserted in the aforesaid hole 12b of the shaft.

In the individual shafts 12a of the cross shaft 12, displacement sensors 151, 152, 153, 154 included in a shaft coupling monitoring apparatus of the invention are disposed in the respective holes 12b thereof. The sensor is adapted to detect any damage, such as flaking and cracks, on a rolling contact surface for the rollers 132, the rolling contact surface defined by the outer periphery of the corresponding shaft 12a. That is, the displacement sensors 151 to 154 are individually disposed in the respective corresponding shafts 12a, thus constituting sensors for detecting the damage on the corresponding rolling contact surfaces of the shafts 12a.

The displacement sensor 151 is connected with a sub-unit 1 by means of a cable 17, the sub-unit 1 removably attached to the aforesaid mounting portion 14a. The displacement sensor is adapted for wireless transmission of the detection results to a base unit to be described hereinlater via the sub-unit 1.

Likewise, the other three shafts 12a are each provided with the lid 14 (not shown) and a sub-unit 2, 3 or 4 connected with each corresponding displacement sensor 152, 153 or 154. The displacement sensors are adapted for wireless transmission of the detection results to the base unit via the respective sub-units 2 to 4.

Figure 3:
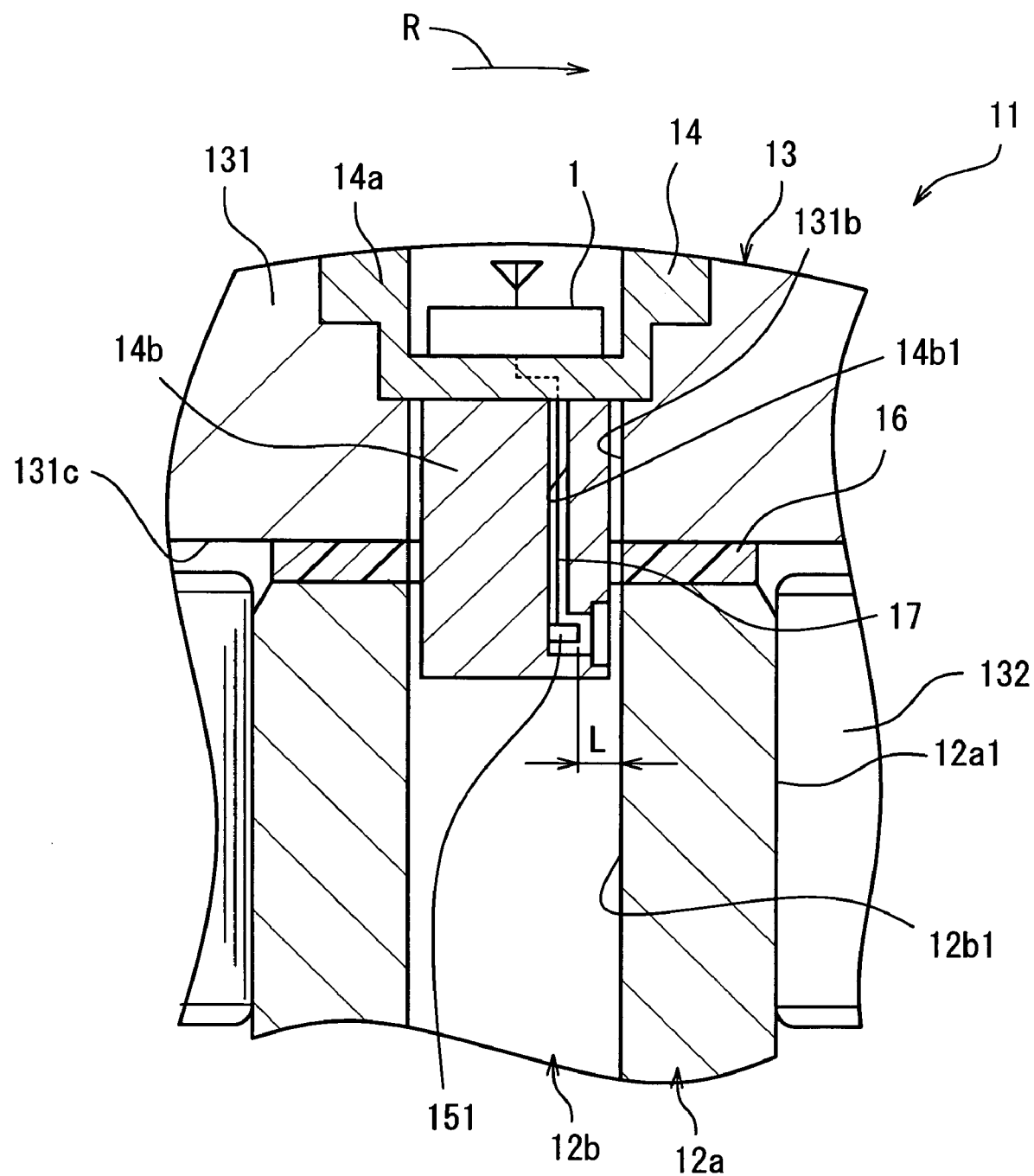
FIG. 3 is an enlarged sectional view showing a displacement sensor of the above shaft coupling monitoring apparatus.

Specifically, as illustrated by FIG. 3, the displacement sensor 151 is disposed at the bearing cup 13 as aligned with a rotational direction of the spider joint 11, which is indicated by an arrow R in the figure. The sensor is located on a line extended in parallel to the rotational direction R and passing through the center of the shaft 12a. The displacement sensor 151 is adapted to pivot (reciprocal pivotal motion) in tandem with the bearing cup 13 pivotally moved relative to the shaft 12a. Specifically, the displacement sensor 151 is accommodated in a sensor-mounting hole 14b1 formed in the support portion 14b of the lid 14 removably mountable to the bearing cup 13 and is fixed to a wall of the sensor-mounting hole 14b1 by means of unillustrated fixing means such as a bracket. Thus, the displacement sensor is pivotally moved in conjunction with the pivotal motion of the cup relative to the shaft 12a. As fixed to the lid 14, the displacement sensor 151 is disposed in the hole 12b of the shaft 12a. The displacement sensor 151 takes measurement on a distance from an inside wall 12b1 of the hole 12b, as indicated by arrows L in the figure, thereby detecting a radial displacement of the shaft 12a as a relative displacement between the shaft 12a and the bearing cup 13. Then, the displacement sensor outputs a detection signal (voltage signal) to the sub-unit 1. Since the axis of the sensor-mounting hole 14b1 is not aligned with the axis of the shaft hole 12b as shown in the figure, the detection signal from the displacement sensor 151 has a sinusoidal waveform (the details of which will be described hereinlater), as periodically varying according to the pivotal motion of the bearing cup 13.

The displacement sensor 151 may employ, for example, a magnetic type sensor equipped with an eddy current probe. The displacement sensor 151 applies a high-frequency magnetic field to a surface layer of the inside wall 12b1 through an opening of the sensor-mounting hole 14b1, so as to determine a variation of impedance of an internal coil caused by an eddy current produced in the surface layer, thereby detecting the radial displacement (relative displacement) of the above shaft 12a, the radial displacement varying according to the pivotal motion of the bearing cup.

The displacement sensor 151 is disposed in correspondence to a range of maximum-load point on the aforesaid rolling contact surface 12a1, the point to which the maximum load is applied during the rotational operation of the spider joint 11. That is, the displacement sensor is disposed in correspondence to the range of maximum load, which exists on the rolling contact surface 12a1 at place in the vicinity of a distal end (the bearing-cup-13 side) of the shaft 12a. The distal end of the shaft 12a is most susceptible to the aforementioned damage. When the shaft 12a is deflected according to the degree of some damage produced on the rolling contact surface 12a1, the sensor detects the aforesaid relative displacement resulting from the deflection, thereby accomplishing the detection of damage.

Figure 4A:
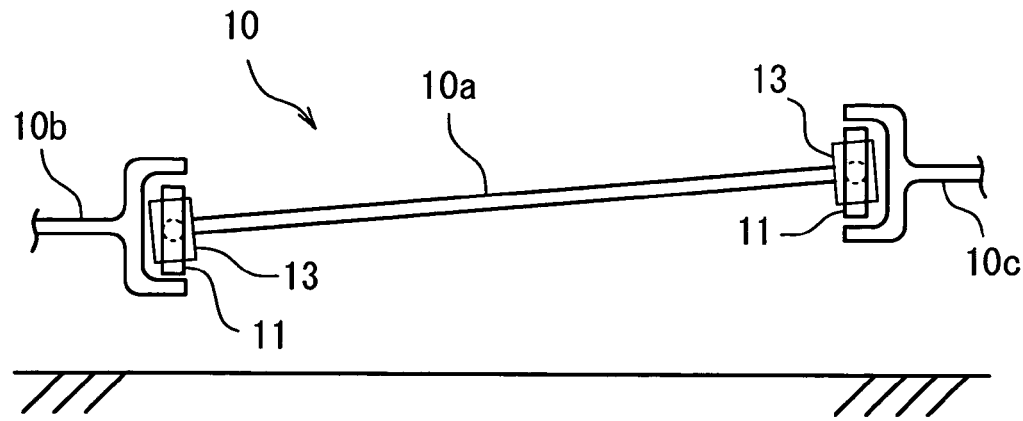
FIG. 4 is a group of diagrams showing a pivotal motion of a spider joint shown in FIG. 2, FIGS. 4(a) and 4(b) individually showing a working angle of the above driving shaft and a bearing cup caused by the working angle to pivotally move relative to the shaft.
Figure 4B:
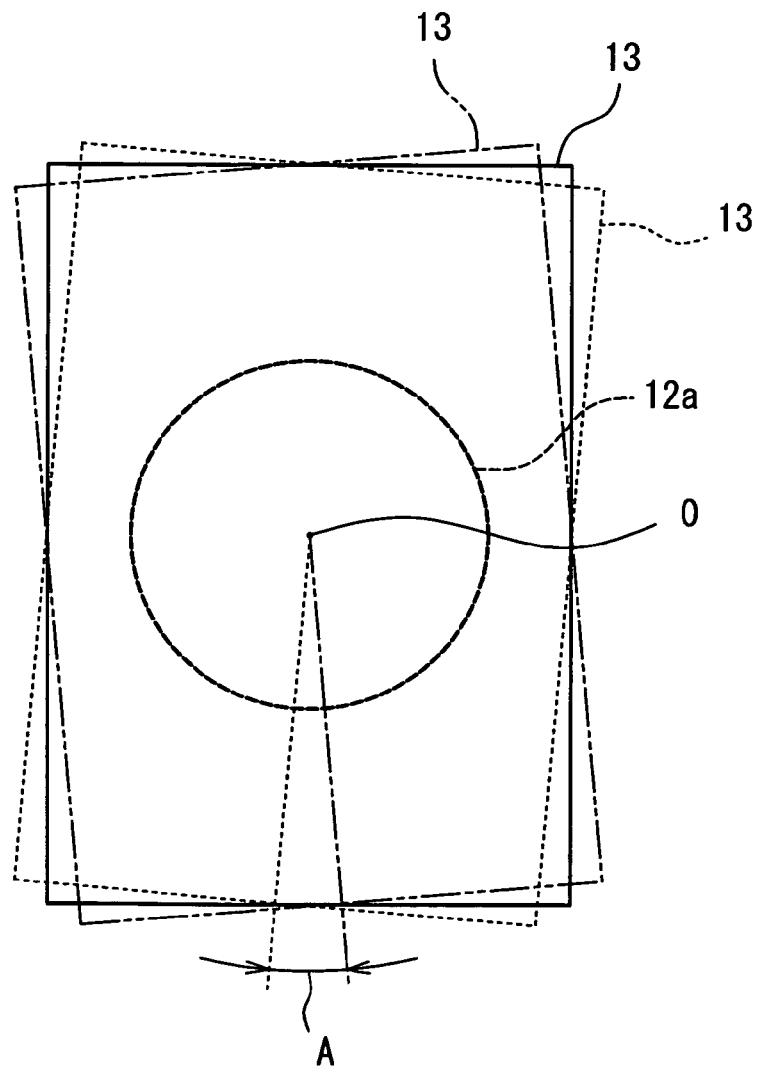

More specifically, the driving shaft 10 is arranged as follows in order to allow the vertical movement of the driven shaft portion 10c on the milling-roll side. The driven shaft portion 10c and the intermediate shaft portion 10a of the driving shaft 10 are interconnected by means of the spider joint 11 which allows the driven shaft portion 10c and the intermediate shaft portion 10a to pivotally move relative to each other in the vertical direction in the range of a predetermined working angle (e.g., 5 deg. in maximum). Therefore, in a case where the intermediate shaft portion 10a is inclined upwardly at the maximum working angle relative to the driving shaft portion 10b, as shown in FIG. 4(a) for example, each of the bearing cups 13 connected with the intermediate shaft portion 10a assumes a position where a right end thereof, as seen in FIG. 4(b), is inclined upwardly relative to the corresponding shaft 12a, as indicated by a chain double-dashed line in the figure. Furthermore, when the intermediate shaft portion 10a assuming the position shown in FIG. 4(a) is rotated through 90 deg. and 180 deg. as maintaining the maximum working angle, the cup 13 is also pivotally moved relative to the shaft 12a in synchronism with the rotating motion of the intermediate shaft portion 10a, as indicated by a solid line and a broken line in FIG. 4(b). The spider joint 11 is arranged to operate as follows. When the joint 11 is rotated in tandem with the driving shaft 10, each of the bearing cups 13 is adapted to pivot (reciprocally pivotally move) with respect to the center O of the shaft 12a in the range (e.g., +5 to −5 deg.) of an angle twice the maximum working angle set for the driving shaft 10.

During the rotational operation of the spider joint 11, the cross shaft 12 having the four shafts 12_is rotated in the same plane in conjunction with the rotation of the driving shaft 10, while the bearing cups 13 mounted to the individual shafts 12 are pivotally moved in the aforementioned manner. Therefore, when the end of the shaft 12a shown in FIG. 4(b) is rotated in a plane perpendicular to the drawing surface and downwardly with respect to the drawing, the maximum-load point on the rolling contact surface 12a1 (FIG. 3) of the shaft 12a, the point subjected to the maximum load from the bearing cup 13, is shifted in conjunction with the pivotal motion of the cup 13 relative to the shaft 12a. Hence, a range of maximum load A is defined as indicated by arrows in FIG. 4(b). A dimension N of the range of maximum load A with respect to the circumferential direction of the rolling contact surface 12a1 may be determined from an equation N=J×M÷360 deg, where J denotes the circumference of the rolling contact surface 12a1, and M denotes the working angle (e.g., 10 deg.) of the spider joint 11, which is twice as great as the maximum working angle of the driving shaft 10.

The torque transmitted from the spider joint 11 to the intermediate shaft portion 10a is specifically transmitted from the shafts 12a to the intermediate shaft portion 10a via the bearing cups 13 disposed at the distal ends of the shafts. Hence, the range of maximum load A is located on the shaft-end side of the rolling contact surface 12a1, whereas the displacement sensor 151 is disposed in the hole 12b in the opposing relation with the shaft-end side of the rolling contact surface 12a1, as shown in FIG. 3. By virtue of such a location of the displacement sensor 151, the sensor 151 is increased in detection accuracy. Specifically, when the shaft 12a is deflected, the distal end of the shaft 12a constitutes a non-confined side (free end) of a cantilever structure wherein the shaft is confined at its side in adjacency to the center of the spider joint 11. Since the displacement sensor 151 is provided on the free-end side, the sensor 151 is capable of detecting the displacement with high accuracies.

Further referring to FIG. 5 to FIG. 7, a specific description is made on the detection signal from the displacement sensor 151. For simplicity, the following description is made on assumption that the intermediate shaft portion 10a continues to rotate as maintaining the maximum working angle and that the pivot angle of the bearing cup 13 relative to the corresponding shaft 12a varies in the range of −5 deg. to +5 deg. It is further assumed that when the bearing cup 13 assume the position indicated by the solid line, the broken line or the chain double-dashed line in FIG. 4(b), the aforesaid pivot angle of the cup 13 is 0 deg., −5 deg. or +5 deg.

Firstly referring to FIG. 6(a), description is made on a detection signal from the displacement sensor 151 when the rolling contact surface 12a1 sustains no damage.

In the case of no damage, the detection signal from the displacement sensor 151 varies in the form of a sinusoidal wave according to the pivotal motion of the bearing cup 13 relative to the shaft 12a, as illustrated by a waveform 50a in FIG. 6(a). The bearing cup pivots in conjunction with the rotational operation of the spider joint 11. More specifically, a detecting direction of the displacement sensor 151 does not necessarily coincide with the center line of the hole 12b through the shaft-12a due to the precisions of assembling the bearing cup 13 to the shaft 12a. Accordingly, the detection signal from the displacement sensor 151 disposed in the sensor-mounting hole 14b1 periodically varies in accordance with only the pivot angle of the bearing cup 13 which pivots in the aforementioned range of −5 deg. to +5 deg. in one revolution of the spider joint 11. When the pivot angle is +5 deg or −5 deg, for example, the detection signal from the displacement sensor 151 is at the maximum value or at the minimum value, thus varying in the sinusoidal waveform, as illustrated by the waveform 50a, which has a period equivalent to one revolution of the above spider joint 11.

Next, description is made on a detection signal outputted from the displacement sensor 151 when the rolling contact surface 12a1 sustains flaking H shown in FIG. 5, for example, as the damage.

In conjunction with the rotational operation of the spider joint 11, the bearing cup 13 is sequentially pivotally moved relative to the center O of the shaft 12a, while the pivot angle of the bearing cup varies in the order of 0 deg., −5 deg., 0 deg. and +5 deg. Since the displacement sensor 151 is fixed to the bearing cup 13, the shaft 12a is moved relative to the detecting direction S of the sensor 151 as shown in FIG. 7(a) to FIG. 7(d). The rolling contact surface 12a1 of the shaft 12a is moved relative to a maximum load point, at which the maximum load is applied from the bearing cup 13 to the shaft 12a, as indicated by an arrow Max in FIG. 7. Therefore, the maximum load point passes over the aforesaid flaking H produced on the rolling contact surface 12a1 while the cup 13 is pivotally moved from a position shown in FIG. 7(a) to a position shown in FIG. 7(b), and from the position of FIG. 7(b) to a position shown in FIG. 7(c).

Since the maximum load point passes over the flaking H in accordance with the pivotal motion of the bearing cup 13, the shaft 12a may be deflected depending upon a positional relation between the maximum load point and the flaking H.

Figure 5A:
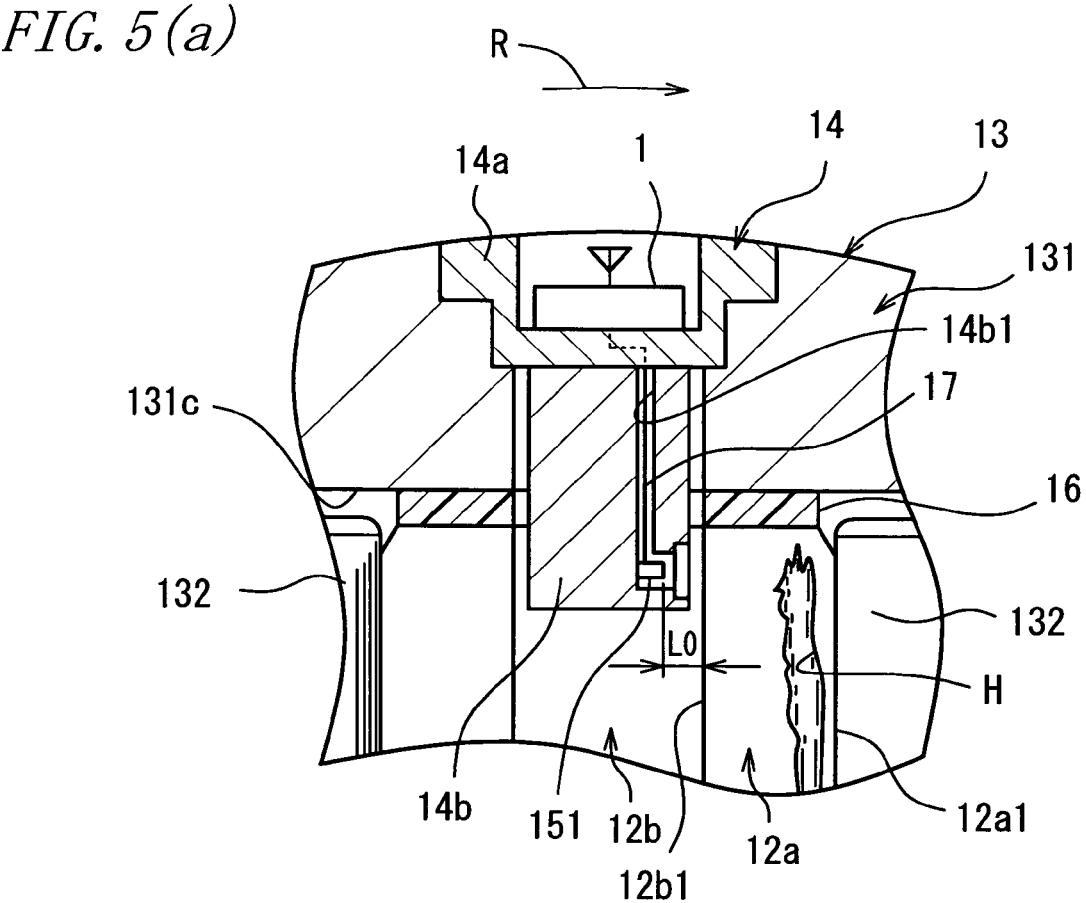
FIG. 5(a) and FIG. 5(b) are diagrams showing an operation of the above displacement sensor when the shaft is not deflected and an operation of the above sensor when the shaft is deflected.

Specifically, when the maximum load point is relatively far away from the flaking H, the shaft 12a is not deflected as shown in FIG. 5(a). Similarly to the case where the shaft does not sustain any flaking H, the displacement sensor 151 takes measurement on the distance L0 from the inside wall 12b1, which distance varies according to the pivot angle of the bearing cup 13. Hence, the sensor outputs the detection signal which is free from fluctuations attributable to the deflection of the shaft.

Figure 5B:
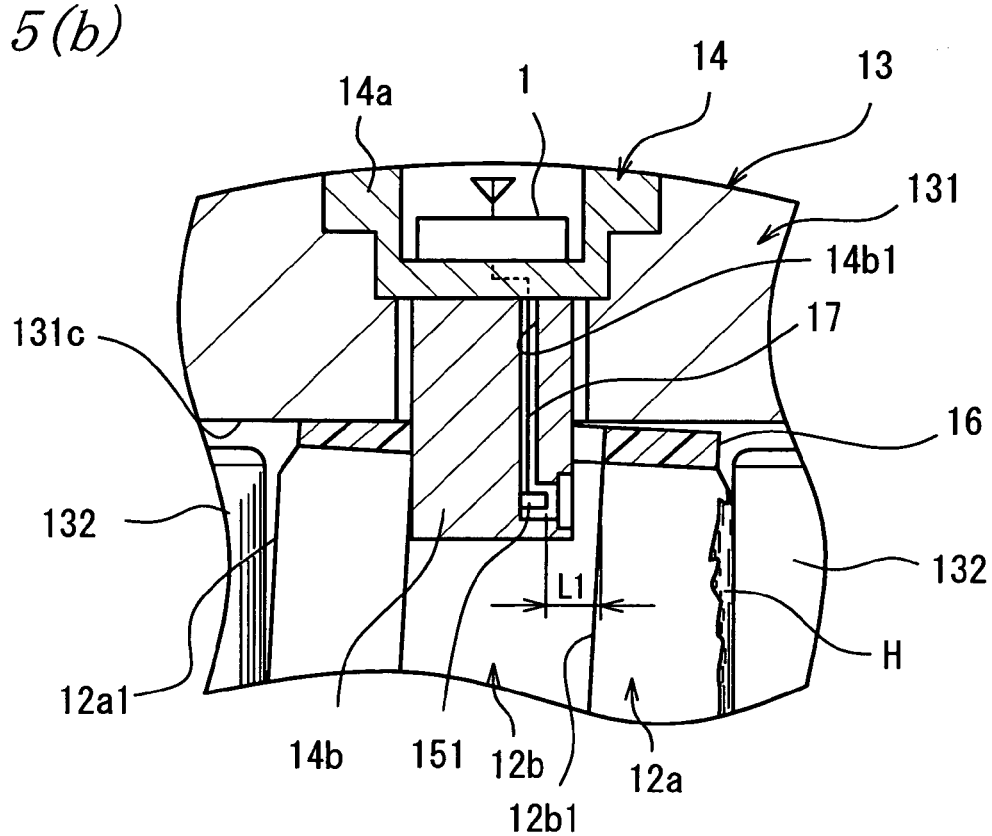
Figure 7A:
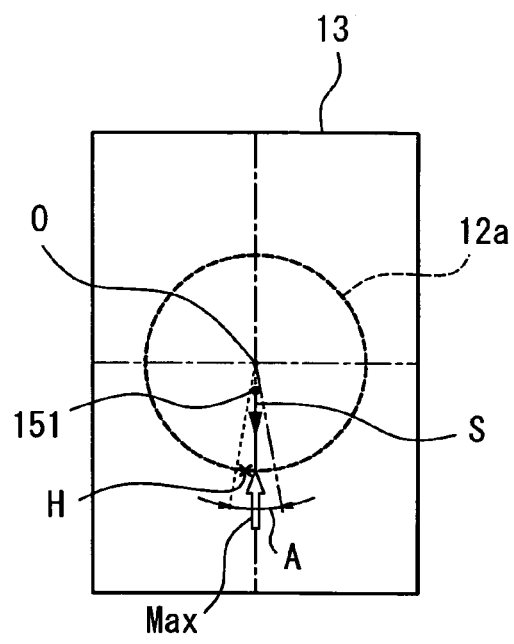
FIG. 7 is a group of diagrams for explaining a method of locating a damaged point by means of the above shaft coupling monitoring apparatus, FIG. 7(a) to FIG. 7(d) each showing a relation of the damaged point with a detection point of the displacement sensor, the detection point varying in accordance with the pivotal motion of the above bearing cup.
Figure 7B:
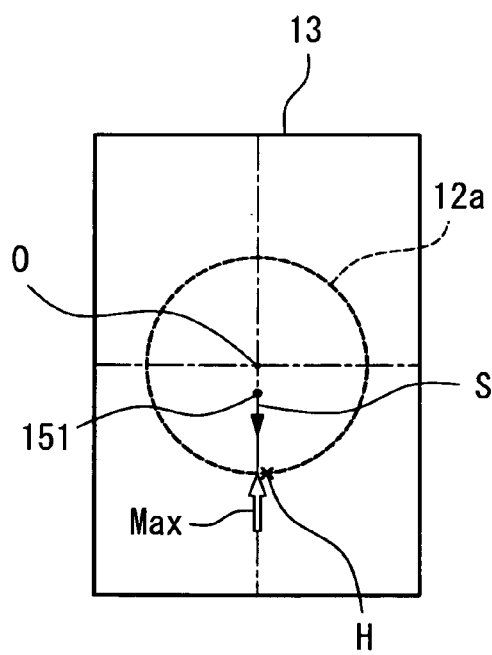
Figure 7C:
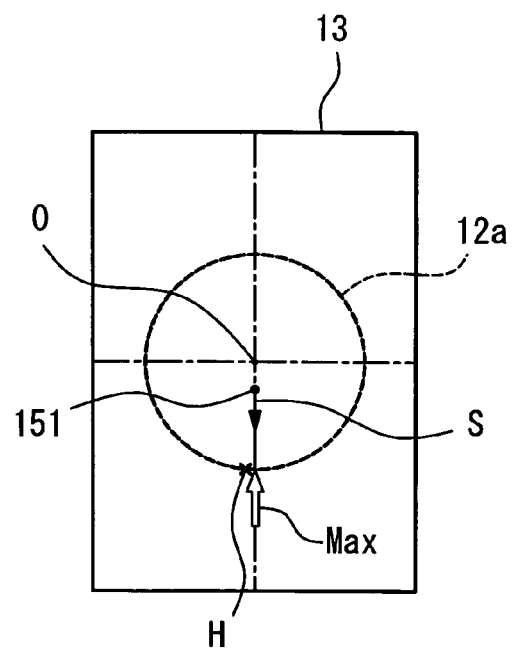
Figure 7D:
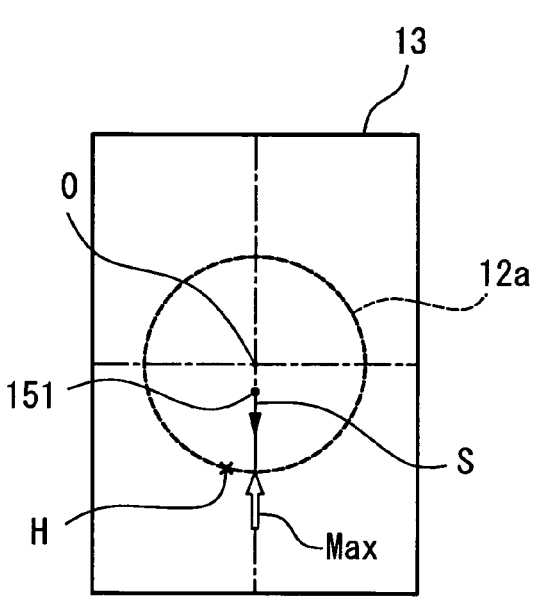

On the other hand, when the maximum load point passes over the flaking H, or when the maximum load point is relatively close to the flaking H before or after the passage over the flaking, the shaft 12a is deflected toward the maximum load point, as shown in FIG. 5(b), so that the end of the shaft is inclined downward to the right as seen in the figure with respect to the rotational direction R of the spider joint 11. The deflection of the shaft 12a varies according to the degree of the depth or extent of the flaking H. When the shaft sustains such a deflection, the displacement detection value provided by the displacement sensor 151 also varies. As shown in FIG. 5(b), the deflection of the shaft 12a results in an increased distance L1 between the displacement sensor 151 and the inside wall 12b1, as compared with the case where the shaft sustains no deflection. As a result, the detection signal from the displacement sensor 151 is also increased in value. As illustrated by a waveform 50b in FIG. 6(b), the detection signal contains an incremental variation wherein the signal value is increased as the shaft is deflected, and the signal value is peaked when the maximum load point passes over the flaking H to cause the maximum deflection of the shaft 12a. Such variations of the output from the displacement sensor 151 may be detected by means of a panel computer or the like (which will be described hereinlater), whereby the occurrence of the flaking H (damage) on the rolling contact surface 12a1, the location of the produced damage, and the degree of the depth or extent thereof may be determined (the details will be described hereinlater).

An alternative constitution to that described above may be made as follows. The displacement sensor 151 is aligned with the center of the shaft hole 12b to fix the distance between the displacement sensor 151 and the inside wall 12b1 irrespective of the variation of the above pivot angle of the bearing cup. Only when the shaft 12a is deflected due to the damage on the rolling contact surface, the displacement sensor 151 may detect a variation of the distance as the result of the shaft deflection.

Figure 8:
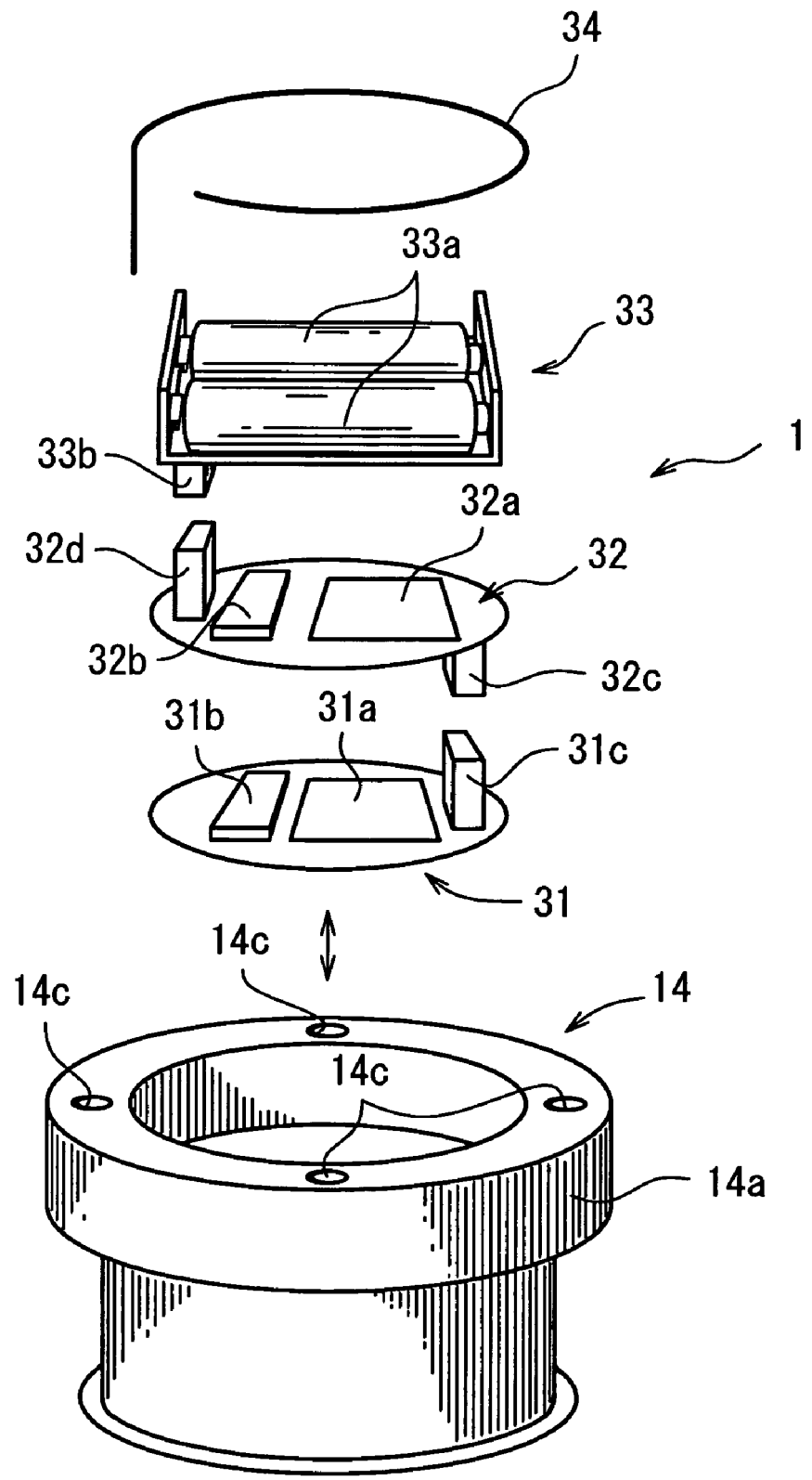
FIG. 8 is a diagram showing an exemplary constitution of an essential part of a sub-unit included in the above shaft coupling monitoring apparatus.

As shown in FIG. 8, the aforesaid sub-unit 1 includes: a sensor board 31 operative to receive the detection signal from the displacement sensor 151 and fixed to a bottom of the mounting portion 14a by means of unillustrated fixing means such as bolt; a wireless board 32 disposed upwardly of the sensor board 31; and a battery power supply 33 disposed upwardly of the wireless board 32. In the sub-unit 1, the boards 31, 32 and the power supply 33 are interconnected in turn by means of detachable connectors. The sub-unit 1 is accommodated in the lid 14 which is mounted in the aforesaid hole 131b by means of screws (not shown) inserted in screw holes 14c. Specifically, the sensor board 31 and the wireless board 32 are electrically interconnected by connecting their respective matching connectors 31c, 32c with each other. The wireless board 32 and the battery power supply 33 are electrically interconnected by connecting their respective matching connectors 32d, 33a with each other. For simplicity, FIG. 8 omits the depiction of the aforesaid support portion 14b. The individual boards 31 and 32 are coated with a mold resin in order to minimize adverse effects, such as from grease and moisture, on electronic devices on these boards 31 and 32. The electronic devices include circuits and the like.

The sensor board 31 includes: a sensor circuit 31a possessing a computation portion such as a DSP imparted with an A/D conversion function to generate sensor-detection signal data by A/D converting the detection signal from the displacement sensor 151; and a power supply circuit 31b for properly distributing DC current to the individual parts of the unit, the DC current derived from, for example, two size-AA batteries included in the above battery power supply 33.

The wireless board 32 includes: a communications circuit 32a such as constituted by a DSP; and a memory 32b for holding data such as programs used by the communications circuit 32a, the above sensor circuit 31a and the like. The wireless board 32 constitutes a data transmitter responsible for wireless transmission of the above sensor-detection signal data outputted from the sensor circuit 31a. The communications circuit 32a is imparted with a transmitting function to output a transmission wave (carrier) having a predetermined frequency, and a modulating function to superimpose the detection signal data on the carrier. The communications circuit 32a further possesses a demodulating function to receive a transmission wave from the base unit 5 to be described hereinlater (FIG. 9) and to demodulate the received wave for extracting an instruction signal contained in the received wave, the instruction signal sent from the base unit 5. The individual parts of the sub-unit 1 are drivably controlled based on the instruction signal. The communications circuit 32a is connected with an antenna 34 disposed upwardly of the battery power supply 33 and in proximity of an open end of the lid 14. The antenna 34 serves to transmit to the outside the transmission wave containing a serial data array of the above sensor-detection signal data. Alternatively, a constitution may also be made such that the antenna 34 is laid along an outside surface of the bearing cup 13.

Similarly to the sub-unit 1, each of the other sub-units 2 to 4 includes the boards and the power supply which are vertically arranged in three separate layers. The sub-units are adapted to transmit the detection signal data from the corresponding displacement sensors 152 to 154.

The above sub-units 1 to 4 and the displacement sensors 151 to 154 are included in the aforementioned shaft coupling monitoring apparatus T. The sub-units 1 to 4 are respectively assigned with ID numbers of serial integers 0, 1, 2, 3 as their identifiers. The communications circuit 32a of the respective sub-units 1 to 4 is designed to affix the assigned ID number to a header of the detection results, provided by the sensor, before sending the transmission wave. Thus, the shaft coupling monitoring apparatus T is adapted to identify the respective sub-units 1 to 4 and the respective displacement sensors 151 to 154 connected with the sub-units 1 to 4.

Figure 9:
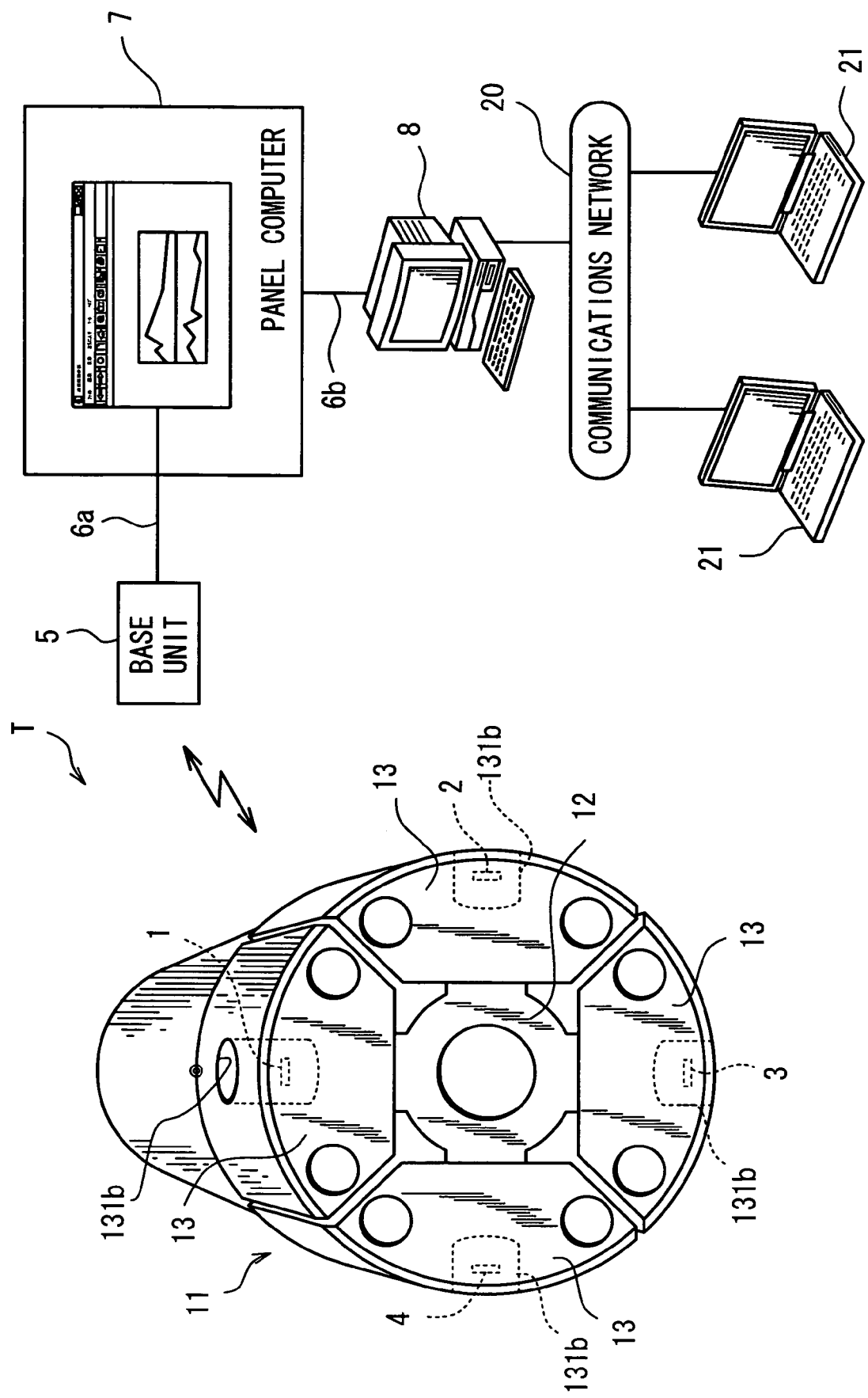
FIG. 9 is a block diagram showing a specific example of a general constitution of the above shaft coupling monitoring apparatus.

As shown in FIG. 9, the shaft coupling monitoring apparatus T includes: the displacement sensors 151 to 154 (FIG. 2); the sub-units 1 to 4 connected with the corresponding sensors 151 to 154; and the base unit 5 for receiving the transmission waves from these sub-units 1 to 4. The base unit 5 is connected with a panel computer 7 via a communication line 6a following, for example, RS232C. The panel computer is disposed in the rolling mill. The panel computer 7 is connected with a personal computer 8 (hereinafter, abbreviated as "PC") by means of a LAN 6b employing, for example, a 10 Base-T line. The PC 8 is installed in a monitor room or the like which is remote from the rolling mill. The PC 8 is adapted for connection with information processor terminals 21 of a manufacturer of the spider joint 11 and a company providing maintenance services of the spider joint, for example, by way of a communications network 20 such as an internet. In the shaft coupling monitoring apparatus T, the sub-units 1 to 4 are mounted to the four spider joints 11 assembled in the two driving shafts 10, whereas the panel computer 7 and the PC 8 are adapted to identify the data pieces transmitted from all the sub-units of the monitoring apparatus T based on the ID numbers. Thus, the monitoring apparatus is adapted to monitor the individual spider joints 11 in respect of each of the shafts 12a.

The panel computer 7 is imparted with a determination/diagnosis function as a computer function thereof. The determination/diagnosis function is to check the sensor-detection signal data sent from the displacement sensors 151 to 154 via the respective sub-units 1 to 4, so as to determine the existence of any damage on each corresponding shaft 12a, the location, the depth, the extent and such of the damaged point.

Specifically, in the case where the sensor detection signal is free from the incremental variation as illustrated by the waveform 50a in FIG. 6A(a), the panel computer 7 determines that the rolling contact surface 12a1 of the corresponding shaft 12a is free from damage.

On the other hand, in the case where the sensor detection signal contains the incremental variation as illustrated by the waveform 50b in FIG. 6(b), or where the inputted signal data contains a value of unexpected, non-periodic incremental variation, the panel computer 7 determines that the above rolling contact surface 12a1 sustains the flaking H (damage). The computer 7 is also adapted to acquire absolute rotational angle information on the spider joint 11 (or the driving shaft 10) by means of an unillustrated position sensor, thereby locating the damaged point on the rolling contact surface 12a1. Specifically, the pivotal motion of the bearing cup 13 and the rotational operation of the spider joint 11 have a correlation. The panel computer 7 refers to a previously inputted and installed table or the like based on the correlation, so as to determine a pivotal status (pivot angle/position) of the bearing cup 13 based on the absolute rotational angle information on the spider joint 11 thus acquired. The panel computer 7 is capable of locating the position of the flaking on the rolling contact surface 12a1 by using the above pivotal status information and the detection results provided by the displacement sensors 151 to 154.

The deflection of the shaft 12a varies according to the depth, extent and the like of the damage. Hence, the panel computer 7 may detect the extent of the damage by detecting a time interval between the values of incremental variations of the above signal data and may also determine the degree of the damage based on the magnitude of the value of the incremental variation.

The panel computer 7 is imparted with the following functions by way of software. The functions include: an information management function to manage information necessary for performing maintenance services on the components of the monitoring apparatus T, the services including, for example, a management of the battery power of the battery power supply 33 of each of the sub-units 1 to 4; and a monitoring function to display predetermined log information items such as the waveforms of the individual sensor-detection signal data pieces and the variations of the above sensor-detection signal data pieces.

In addition to the above computer functions possessed by the panel computer 7, the PC 8 is further imparted with a server function to store data including input detection data, the results of diagnosis based on the input data and the like, and to operate as a Web server to provide the above stored data to the other information processor terminals 21.

According to Embodiment 1 constituted as described above, the displacement sensors 151 to 154 are disposed in the respective shafts 12a of the cross shaft 12, whereas each of the displacement sensors 151 to 154 takes measurement on the distance from the inside wall 12b1, thereby detecting the radial displacement (relative displacement) between the corresponding shaft 12a and bearing cup 13 with respect to the radial direction of the shaft 12*a*. When the shaft 12*a* is deflected according to the damage produced on the rolling contact surface 12*a*1, the panel computer 7 or the PC 8 determines on the existence of damage on the rolling contact surface 12*a*1 and determines the extent, the depth and the like of the damage (the degree of the progress of the damage) based on the detection results provided by any of the displacement sensors 151 to 154, the detection results varied by the deflection. Thus, high-accuracy monitoring/diagnosis of the spider joint 11 may be provided in respect of each of the shafts 12*a*. The monitoring/diagnosis include the detection of any damage on the rolling contact surface 12*a*1 in an early stage. Accordingly, a proper maintenance service may be conducted in a correct timing based on the highly accurate diagnosis results, without previously carrying out the periodical inspection operations which involve the overhaul of the spider joint 11.

According to Embodiment 1, the individual displacement sensors 151 to 154 are disposed on the line extended in parallel to the rotational direction R of the spider joint 11 and passing through the center O of the respective shafts 12*a* as well as on the side of the aforesaid range of maximum load A. Therefore, these displacement sensors 151 to 154 are each located in the deflection direction of the shaft 12*a* deflected due to the damage produced on the rolling contact surface 12*a*1. Accordingly, the individual displacement sensors 151 to 154 are capable of detecting the deflection-induced displacement/variation with the highest sensitivity, thus accomplishing a more accurate detection of the damage.

According to Embodiment 1, the displacement sensors 151 to 154 are each disposed in the grease-passage hole 12*b* formed in the corresponding shaft 12*a* in coaxial relation with the shaft 12*a*. The displacement sensors each detect the relative displacement by taking measurement on the distance from the inside wall 12*b*1 of the hole. In this manner, the displacement sensors 151 to 154 each detect the relative displacement as disposed in the shaft itself which is deflected due to the damage produced on the rolling contact surface 12*a*1 thereof. Hence, the sensor may be increased in the detection accuracy. Furthermore, the grease-passage hole 12*b* is utilized to negate the need for forming a hole, recess or the like to accommodate the respective displacement sensors 151 to 154 in each corresponding shaft. This facilitates the installation of the sensors 151 to 154 in the spider joint 11.

Embodiment 2

Figure 10:
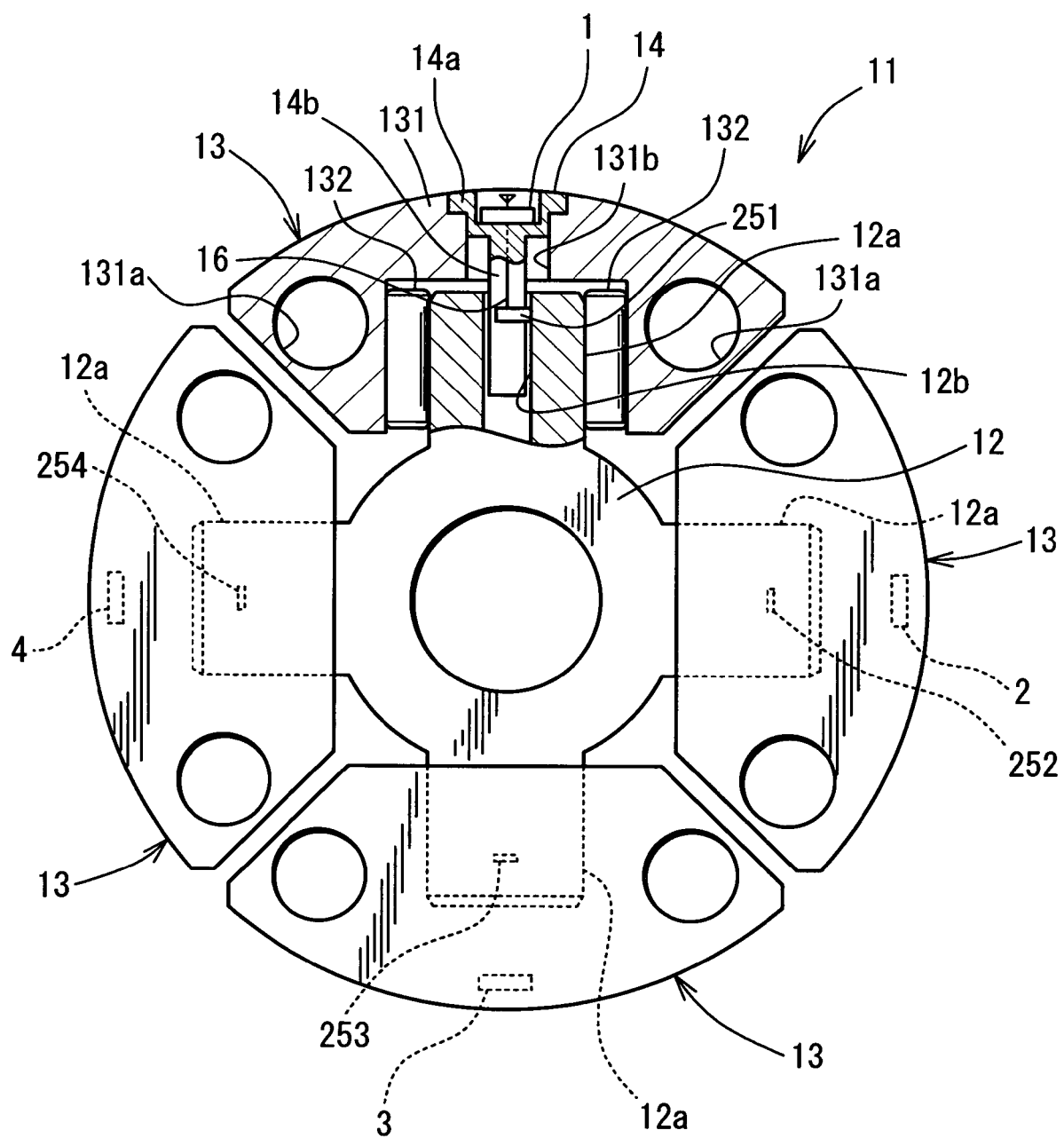
FIG. 10 is a diagram (including a partial sectional view) showing an essential part of a shaft coupling monitoring apparatus according to another embodiment of the invention as viewed in the axial direction of the driving shaft.

FIG. 10 is a diagram (including a partial sectional view) showing an essential part of a shaft coupling monitoring apparatus according to another embodiment of the invention, as viewed in the axial direction of the driving shaft. Referring to the figure, Embodiment 2 principally differs from Embodiment 1 in that the displacement sensors 151 to 154 are replaced by ultrasonic sensors disposed in the respective shafts. The ultrasonic sensor is adapted to output an ultrasonic wave toward the rolling contact surface 12*a*1 of the shaft 12*a* and to receive the ultrasonic wave reflected from the rolling contact surface 12*a*1. Those components equivalent to those of Embodiment 1 are represented by the same reference characters, respectively, and the description thereof is dispensed with.

As shown in FIG. 10, the individual shafts 12*a* of the cross shaft 12 are provided with ultrasonic sensors 251, 252, 253, 254 in the respective holes 12*b* thereof. The ultrasonic sensors are included in the shaft coupling monitoring apparatus T of the invention and are each designed to detect any damage, such as flaking and cracks, on the corresponding rolling contact surface 12*a*1 for the rollers 132. The rolling contact surface 12*a*1 utilizes the outer periphery of the shaft 12*a*.

Figure 11A:
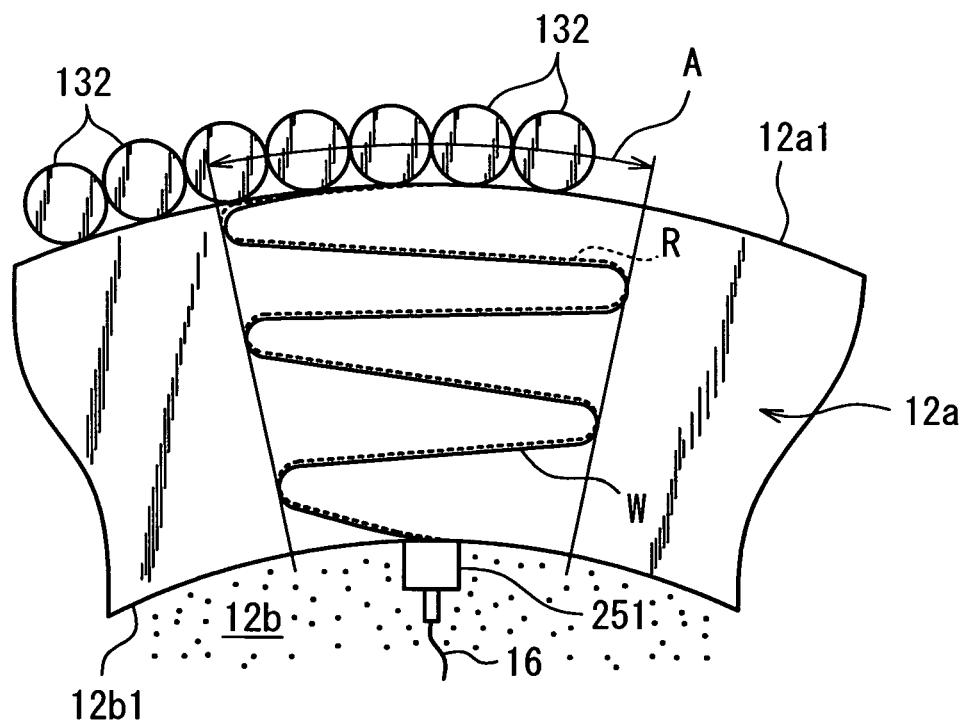
FIG. 11 is a group of diagrams showing an ultrasonic sensor of the shaft coupling monitoring apparatus shown in FIG. 10, FIG. 11(a) and FIG. 11(b) illustrating specific examples of the operations of the sensor when there is no damage and when there is some damage.
Figure 11B:
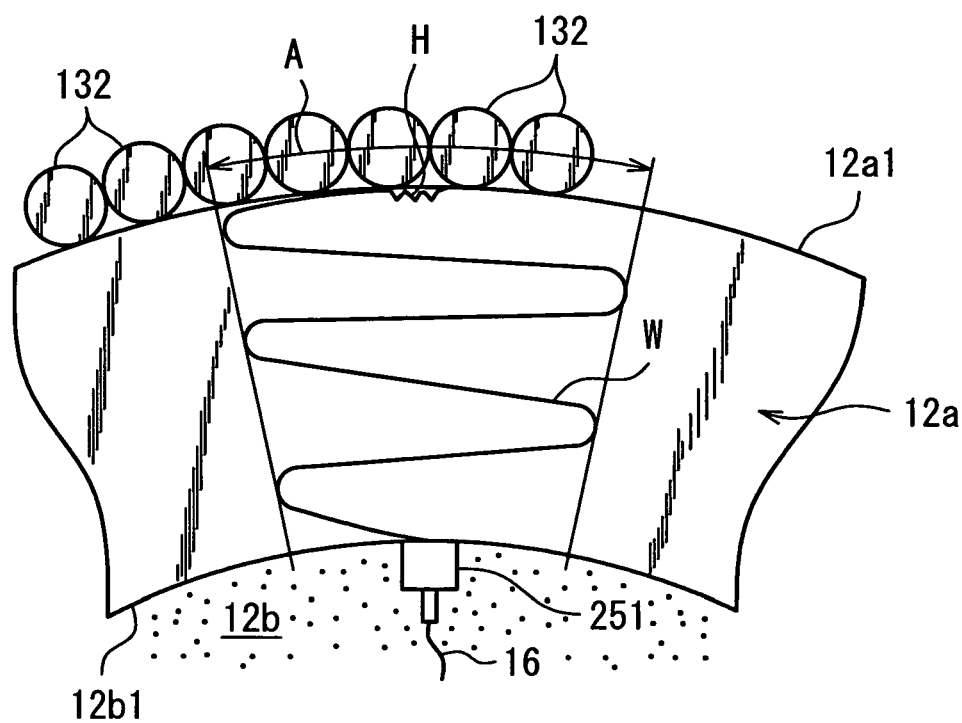

Specifically, the ultrasonic sensor is constituted as follows. As illustrated by FIG. 11, the ultrasonic sensor 251 is accommodated in the hole 12*b* as an installation space and holds a sensor end portion in close contact against the inside wall 12*b*1 of the hole 12*b*, the sensor end portion including an ultrasonic-wave output portion and an ultrasonic-wave receiving portion. In this state, the sensor outputs an ultrasonic outgoing wave W toward the rolling contact surface 12*a*1 defined by the outer periphery of the shaft 12*a* and receives an ultrasonic reflective wave R from the rolling contact surface 12*a*1. The ultrasonic sensor 251 is fixed to the shaft 12*a* by means of mounting means such as a bracket (not shown). The sensor is disposed in the hole 12*b* without allowing the grease to be interposed between the sensor end portion thereof and the inside wall 12*b*1, the grease represented by dots in the figure.

The ultrasonic sensor 251 includes a piezoelectric device for generating the ultrasonic wave and a piezoelectric device for receiving the ultrasonic wave. During the rotational operation of the spider joint 11, the sensor is capable of outputting such an ultrasonic wave as to cover the overall range of maximum load A (FIG. 4) in one period. The range of maximum load A is included in an area of the rolling contact surface 12*a*1 which is subjected to the maximum load, and is located on the rolling contact surface 12*a*1 at place in the vicinity of the distal end of the shaft 12*a* (the bearing-cup-13 side), where the damage is most likely to occur. Similarly to the displacement sensor 151, the ultrasonic sensor 251 is disposed in the hole 12*b* in opposing relation with the shaft-end side of the rolling contact surface 12*a*1 (FIG. 3) in order to cover the aforesaid range of maximum load A (FIG. 10).

As shown in FIG. 11, the ultrasonic sensor 251 outputs the aforesaid outgoing wave W toward the rolling contact surface 12*a*1 as the ultrasonic wave capable of covering the overall range of maximum load A in one period. The outgoing wave W is composed of a transverse ultrasonic wave having an amplitude equal to the aforesaid circumferential dimension N or a longitudinal ultrasonic wave having a spreading width equal to the above dimension N. The outgoing wave W has a selected frequency such that the ultrasonic wave may not be significantly attenuated as traveling in a propagation path through the shaft 12*a* as a propagation medium of the ultrasonic wave.

In a case where the rolling contact surface 12*a*1 does not sustain any damage (flaking H) as shown in FIG. 11(*a*), the outgoing wave W outputted from the wave output portion of the ultrasonic sensor 251 toward the rolling contact surface 12*a*1 is reflected by the rolling contact surface 12*a*1 so that the wave reflected as the reflective wave R is received by the wave receiving portion of the sensor 251 after the lapse of a predetermined period of time from the wave output. Then, the ultrasonic sensor 251 outputs a detection signal (voltage signal) according to the received reflective wave R to the sensor circuit 31*a* (FIG. 8) of the aforesaid sub-unit 1.

On the other hand, in a case where the rolling contact surface 12*a*1 sustains some damage (flaking H) as shown in FIG. 11(*b*), the outgoing wave W outputted from the wave output portion of the ultrasonic sensor 251 toward the rolling contact surface 12*a*1 is diffused at the flaking H. Therefore, the wave receiving portion of the ultrasonic sensor 251 cannot receive the reflective wave R at all, as shown in FIG. 11(*b*). Otherwise, the sensor 251 may receive some of the diffused ultrasonic wave after the lapse of the predetermined period of time. The received reflective wave R is much less than the wave received in the case where the flaking H does not occur.

In this manner, the reflective wave R received by the wave receiving portion of the ultrasonic sensor 251 varies depending upon the existence of the flaking H. Accordingly, the detection signal outputted from the sensor 251 to the sensor circuit 31a also varies in a similar manner.

Figure 12A:
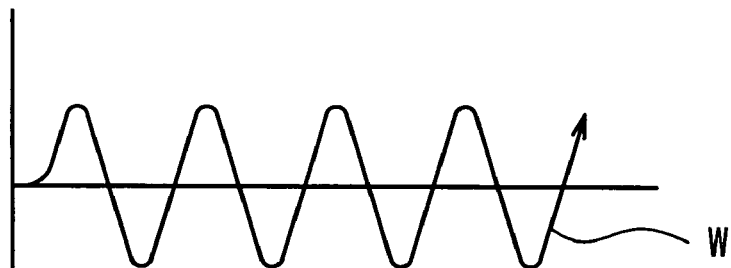
FIG. 12 is a group of waveform charts showing specific operating waveforms of the above ultrasonic sensor, FIG. 12(a) showing a waveform of an outgoing wave from the sensor, FIG. 12(b) showing a waveform of a reflective wave from a damage-free outer periphery (rolling contact surface) of the shaft of the above spider joint, FIG. 12(c) showing a waveform of a reflective wave actually received by the sensor when the above rolling contact surface of the shaft is free from damage.
Figure 12B:
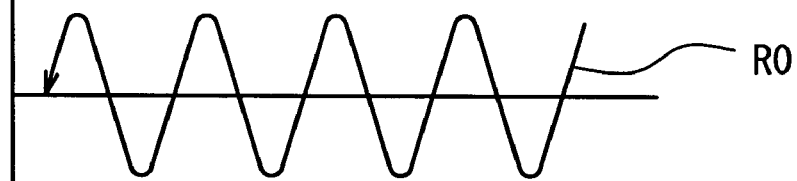
Figure 12C:
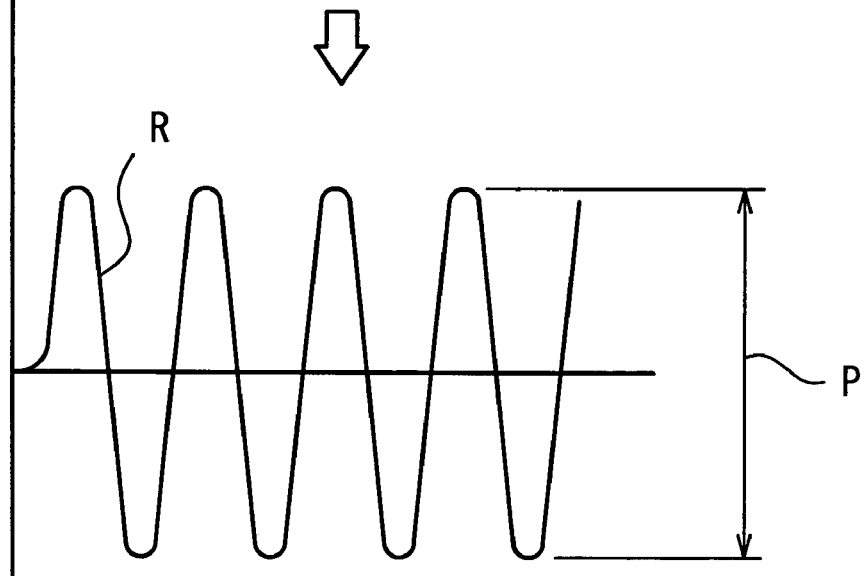

In the ultrasonic sensor 251, the phase of the outgoing wave W is adjusted before outputted such that the ultrasonic reflective wave R received by the ultrasonic sensor 251 may be amplified, as shown in FIG. 12. As shown in FIG. 12(a) and FIG. 12(b), the outgoing wave W is in phase with an ultrasonic reflective wave RO reflected from the rolling contact surface 12a1 which does not sustain any damage. When the rolling contact surface 12a1 is free from the damage, the ultrasonic sensor 251 receives the reflective wave R having a maximum peak value P (outgoing wave W×2-amount of wave transmitted to rollers) due to interference between the outgoing wave S and the reflective wave RO, as shown in FIG. 12(c).

The above sub-unit 1 operates similarly to that of Embodiment 1. The sensor circuit 31a of the sub-unit subjects the detection signal from the ultrasonic sensor 251 to the predetermined data processing such as A/D conversion, so as to output the transmission wave to the base unit 5 via the antenna 34, the transmission wave including the serial data array of the above detection signal data. The base unit 5, in turn, transmits the serial data array to the panel computer 7 (see FIG. 8 and FIG. 9).

As shown in FIG. 10, the other three shafts 12a are also provided with the ultrasonic sensors 252, 253, 254 and the sub-units 2, 3, 4 connected therewith, respectively. Thus, the apparatus is adapted to transmit the respective detection signal data pieces (results) from the four sub-units 1 to 4 to the panel computer 7. These sub-units 1 to 4 and the ultrasonic sensors 251 to 254 are included in the above shaft coupling monitoring apparatus T, wherein the individual sub-units 1 to 4 and ultrasonic sensors 251 to 254 may be identified based on the identifiers (ID numbers) assigned to the respective sub-units 1 to 4.

By way of the determination/diagnosis function as the computer function thereof, the panel computer 7 or the PC 8 checks the detection signal data pieces supplied from the respective ultrasonic sensors 251 to 254 for determining on the existence of damage on the corresponding shafts 12a. After the output of the ultrasonic outgoing wave W from the ultrasonic-wave output portion of each of the sensors 251 to 254, the panel computer 7 or the PC 8 monitors the variations of the ultrasonic reflective wave R, such as the variations of the maximum peak value thereof, the reflective wave received by the corresponding wave receiving portion. When the maximum peak value so monitored reaches a value (outgoing wave S×2-"amount of wave transmitted to rollers") shown in FIG. 12(c), the panel computer or the PC determines that the rolling contact surface 12a1 as a monitor target is free from damage. When, on the other hand, the maximum peak value so monitored does not reach the above twofold value, it is determined that the rolling contact surface 12a1 as the monitor target sustains some damage.

According to Embodiment 2 constituted as described above, the individual shafts 12a of the cross shaft 12 contain therein the ultrasonic sensors 251 to 254, whereas the individual ultrasonic sensors 251 to 254 output the ultrasonic wave toward the corresponding rolling contact surfaces 12a1 of the shafts 12a and receive the reflective wave R from the rolling contact surfaces 12a1. Based on the variations of the reflective wave R, the panel computer 7 or the PC 8 determines on the occurrence of damage on the rolling contact surface 12a1 or determines the degree of progress of the damage. Similarly to Embodiment 1, the monitoring apparatus of Embodiment 2, as applied to the spider joint incorporated in the driving shaft such as of the rolling mill, is also capable of providing the high-accuracy monitoring/diagnosis of the spider joint 11 in respect of each of the shafts 12a, the diagnosis including the detection of the damage on the rolling contact surface 12a1. In addition, the damage may be detected in its early stage. As a result, the proper maintenance service may be conducted in a correct timing based on the highly accurate diagnosis results, which may be obtained without previously carrying out the periodical inspection operations which involve the overhaul of the spider joint 11.

According to Embodiment 2, the ultrasonic sensors 251 to 254 each output the outgoing wave W as keeping the outgoing wave W in phase with the ultrasonic reflective wave RO reflected from the rolling contact surface 12a1 free from damage. Hence, the sensors 251 to 254 may each receive the ultrasonic wave increased in amplitude, so that the sensors may achieve increased accuracies of the detection of damage on the corresponding rolling contact surfaces 12a1.

According to Embodiment 2, the ultrasonic sensors 251 to 254 each output the ultrasonic wave toward the rolling contact surface 12a1 as closely contacted against the inside walls 12b1 of the hole 12b. This obviates the formation of an interface on an ultrasonic-wave propagation path between each of these sensors 251 to 254 and each corresponding rolling contact surface 12a1. Therefore, the ultrasonic sensor is prevented from encountering the change of the propagation path due to the ultrasonic wave refracted by the interface. This ensures that the ultrasonic sensor provides an exact ultrasonic sensing in respect of a desired point on the rolling contact surface 12a1.

Embodiment 3

FIG. 13 is a group of diagrams showing an ultrasonic sensor of a shaft coupling monitoring apparatus according to another embodiment of the invention. Referring to the figure, Embodiment 3 principally differs from Embodiment 2 in that the fixing place of the ultrasonic sensor is shifted from the shaft side to the bearing-cup side. Those components equivalent to those of Embodiment 1 are represented by the same reference characters, respectively, and the description thereof is dispensed with.

Referring to FIG. 13, a sensor according to the embodiment is disposed in each shaft 12a as follows. The ultrasonic sensor 251, for example, is disposed in the hole 12b as mounted to a fixing member 14d attached to the support portion 14b (FIG. 10) of the lid 14 so as to be fixed to the bearing cup 13 via the lid 14. The ultrasonic sensor 251 of the embodiment is spaced away from the inside wall 12b1 of the hole 12b. In this state, the ultrasonic sensor outputs the ultrasonic outgoing wave W toward the rolling contact surface 12a1 by means of the wave output portion and receives the reflective wave R from the rolling contact surface 12a1 by means of the wave receiving portion. As described above, the ultrasonic sensor 251 is spaced away from the inside wall 12b1, so that the grease having a different density from that of the shaft 12a is interposed between the sensor and the inside wall. It is therefore preferred that the ultrasonic sensor 251 outputs a longitudinal ultrasonic wave rather than a transverse ultrasonic wave. The outgoing wave composed of the longitudinal ultrasonic wave does not form a surface acoustic wave. In contrast, the outgoing wave W composed of the transverse ultrasonic wave involves a fear of not being propagated to the rolling contact surface 12a1, because the transverse ultrasonic wave forms the surface acoustic wave as passing through the interface between the substances of different densities. It is also preferred that the ultrasonic sensor 251 is disposed in close proximity to the inside wall 12b1 to define a small gap between the sensor 251 and the inside wall 12b1.

Figure 13A:
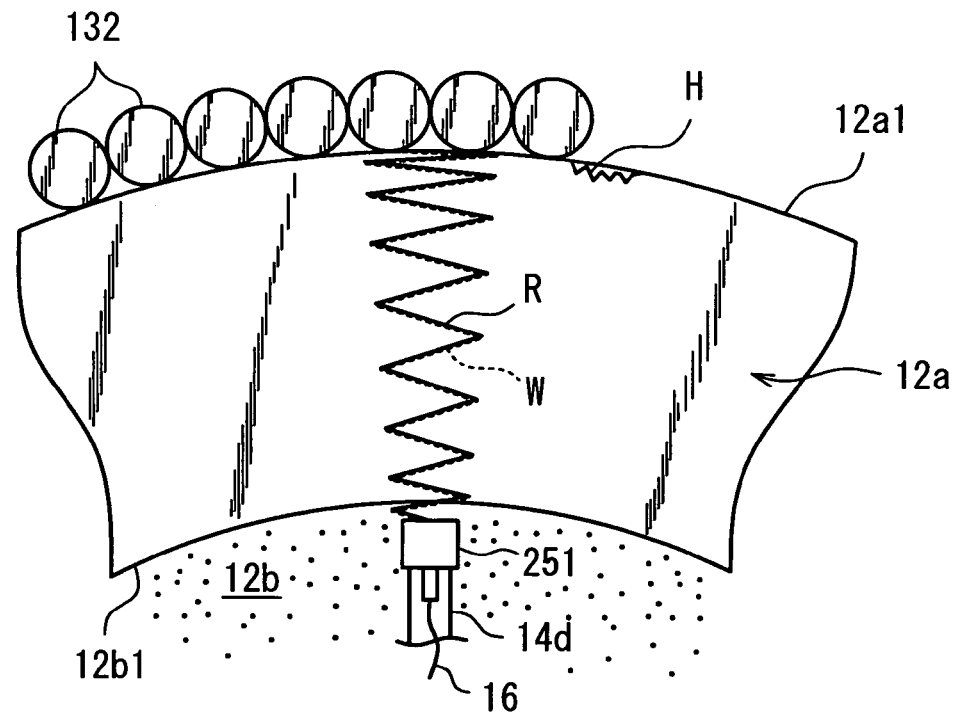
FIG. 13 is a group of diagrams showing an ultrasonic sensor of a shaft coupling monitoring apparatus according to another embodiment of the invention, FIG. 13(a) and FIG. 13(b) illustrating specific examples of the operations of the sensor when there is no damage and when there is some damage.
Figure 13B:
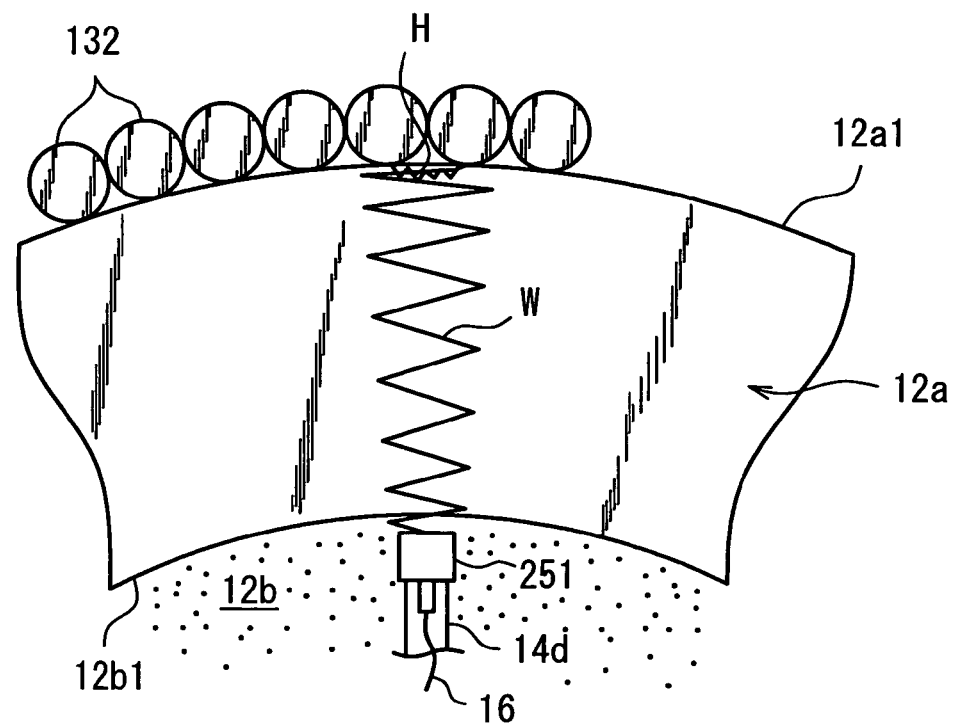
Figure 14A:
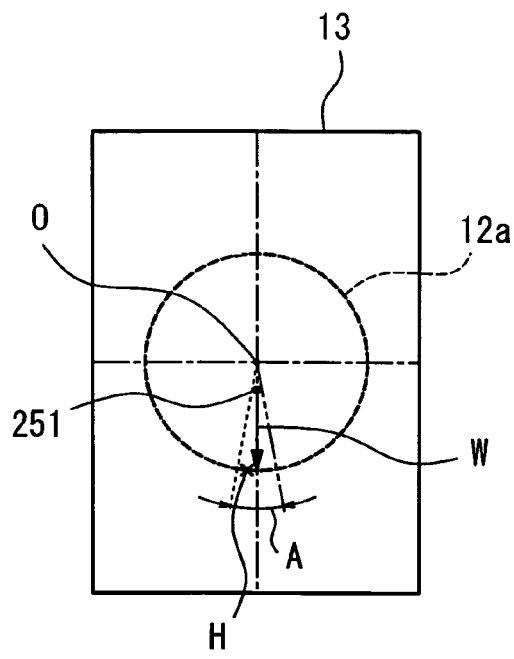
FIG. 14 is a group of diagrams for explaining a method of locating a damaged point by means of the shaft coupling monitoring apparatus shown in FIG. 13, FIG. 13(a) to FIG. 13(d) each showing a relation of the damaged point with a detection point of the ultrasonic sensor, the detection point varying in accordance with the pivotal motion of the above bearing cup.
Figure 14B:
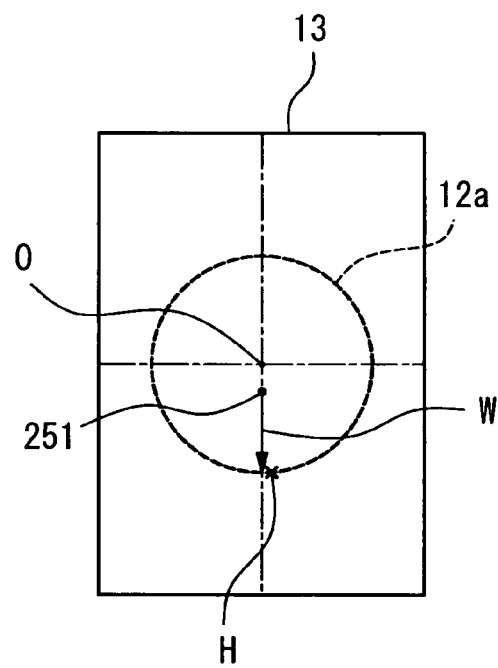
Figure 14C:
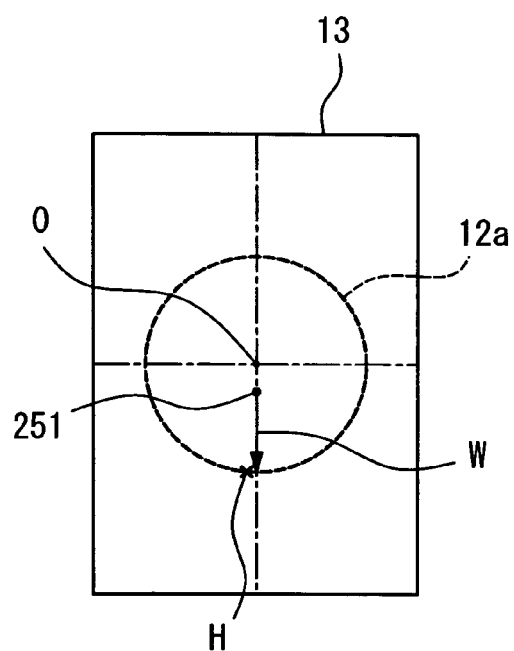
Figure 14D:
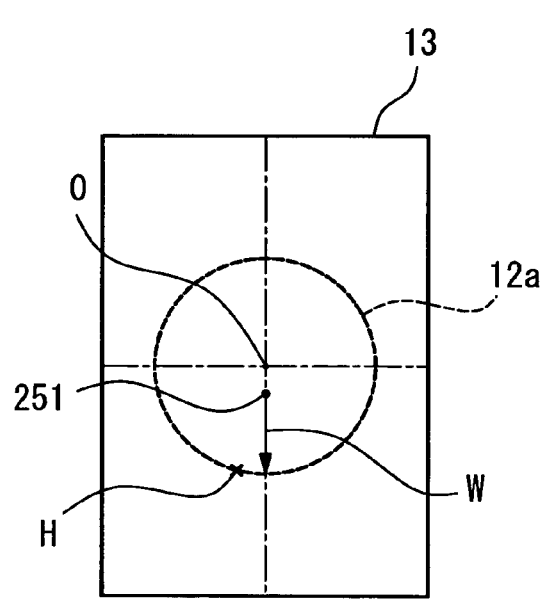
Figure 15:
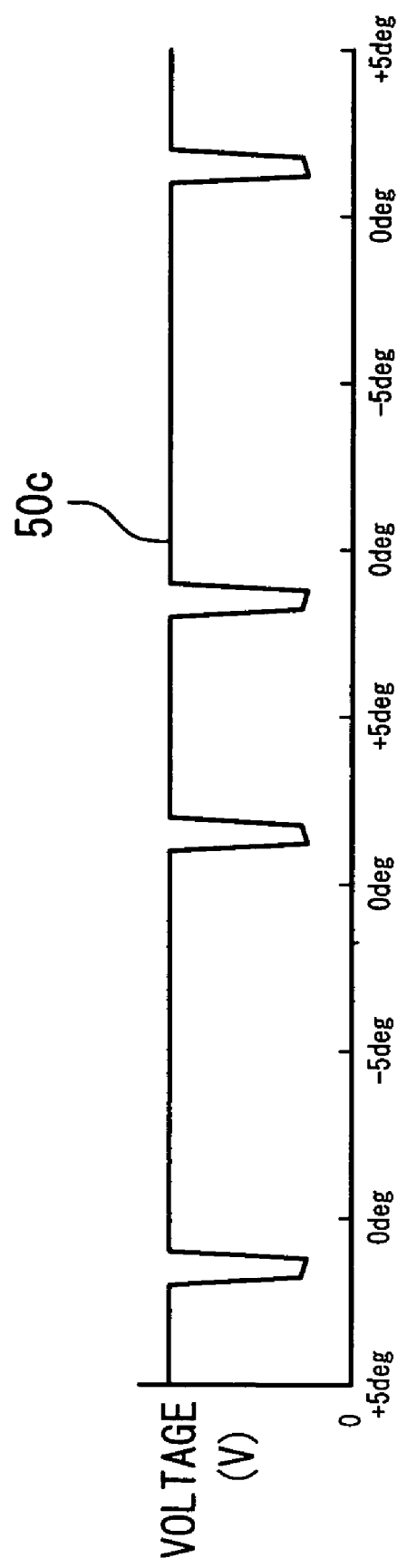
FIG. 15 is graph showing a specific waveform of a detection signal inputted from the ultrasonic sensor to a panel computer shown in FIG. 9.

According to Embodiment 3 constituted as described above, the ultrasonic sensor 251 is fixed to the bearing cup 13. Therefore, when the cup 13 is pivotally moved relative to the corresponding shaft 12a in conjunction with the rotation of the driving shaft 10, an incidence point of the outgoing wave W from the sensor 251 or an ultrasonic sensing point on the rolling contact surface 12a1 is also pivotally moved (reciprocally pivotally moved) in the aforesaid range of maximum load A. In a case where the rolling contact surface 12a1 does not sustain any flaking H, as shown in FIG. 13(a), the outgoing wave W outputted from the wave output portion of the ultrasonic sensor 251 toward the rolling contact surface 12a1 is reflected by the corresponding rolling contact surface 12a1 so as to be received as the reflective wave R by the receiving portion of the sensor 251 after the lapse of a predetermined period of time from the wave output, just as in Embodiment 2. In conjunction with the pivotal motion of the bearing cup 13, the irradiation point of the ultrasonic sensor 251 is pivotally shifted rightward from place shown in FIG. 13(a) to place shown in FIG. 13(b). In this state, the outgoing wave W outputted from the wave output portion toward the rolling contact surface 12a1 is diffused by the flaking H on the rolling contact surface 12a1. Hence, the sensor 251 cannot receive the normal reflective wave R, thus detecting the occurrence of the flaking H (damage). Consequently, the detection signal transmitted from the ultrasonic sensor 251 to the panel computer 7 and indicating the occurrence of the flaking H has a waveform such as illustrated by a waveform 50c in FIG. 15 wherein the voltage value drops in correspondence to only the detection point of the flaking H.

According to Embodiment 3 of the invention, the sensing point of the ultrasonic sensor 251 is pivotally moved in the range of maximum load A. In contrast to Embodiment 2, the sensor is not required to output the high-amplitude/high-power ultrasonic wave capable of covering the overall range of maximum load A in one period. Hence, the sensor of the embodiment is capable of accomplishing the damage detection by way of the ultrasonic wave having a lower output than that of Embodiment 2.

In addition, the above panel computer 7 or the PC 8 is also capable of locating the damaged point on the rolling contact surface 12a1 by detecting the number of rotations of the spider joint 11 (driving shaft 10). Specifically, while the bearing cup 13 is sequentially pivotally moved relative to the center of the shaft 12a, the motion of the shaft 12a relative to the outgoing wave W from the ultrasonic sensor 251 is made as shown in FIG. 14(a) to FIG. 14(d), because the ultrasonic sensor 251 is fixed to the bearing cup 13. On the other hand, the flaking H is also relatively shifted from a position shown in FIG. 14(a) to a position shown in FIG. 14(b), and from the position of FIG. 14(b) to a position shown in FIG. 14(c). During one period in which the sensing point is pivotally moved in the range of maximum load A, the sensor 251 experiences two events of inability to receive the reflective wave R and of reception of a reflective wave R having a much lower value than the normal maximum peak value (FIG. 12(c)). Hence, the panel computer 7, for example, is designed to acquire absolute rotational angle information on the spider joint 11 (or the driving shaft 10) by means of an unillustrated position sensor such as to locate the damaged point on the rolling contact surface 12a1. That is, the pivotal motion of the bearing cup 13 is correlated with the rotational operation of the spider joint 11. The panel computer 7 may refer to a previously inputted and installed table or the like based on the correlation, so as to determine a pivotal status (pivot angle/position) of the bearing cup 13 based on the absolute rotational angle information on the spider joint 11 thus acquired. Then, the panel computer 7 may locate the position of the flaking on the rolling contact surface 12a1 by using the above pivotal status information and the detection results provided by the ultrasonic sensors 251.

While the above description illustrates the case where the invention is applied to the spider joint incorporated in the driving shaft of the rolling mill, the invention is applicable to any arrangement wherein the sensor for detecting the damage on the rolling contact surface defined by the outer periphery of the shaft is disposed in the shaft. The invention may also be applied to, for example, a monitoring apparatus for spider joint in a driving shaft incorporated in a railroad vehicle.

While the forgoing description illustrates the constitution wherein the sub-unit is provided for transmitting the detection result provided by the displacement sensor or the ultrasonic sensor to the external apparatus, an alternative constitution may be made as follows. A memory for storing the detection result provided by the sensor is disposed in place of the sub-unit, while the monitoring of damage is carried out based on the detection result stored in the memory. However, the constitution wherein the sub-units are used for sequentially transmitting the sensor detection results is more preferred from the viewpoint of detecting the damage on the rolling contact surface on a real-time basis.

While the foregoing description illustrates the constitution wherein the panel computer or the PC performs the process to determine on the existence of damage or to determine the degree of the progress of damage based on the detection result provided by the displacement sensor or the ultrasonic sensor, the invention is not limited to this. Alternatively, a data processor such as a DSP provided in the aforementioned sensor circuit may perform the above determination process.

While the description of Embodiment 1 illustrates the constitution wherein the displacement sensor is fixed to the lid removably mountable to each of the bearing cups in order to take measurement on the distance from the inside wall of the hole serving as the grease passage (or the radial displacement of the shaft), the fixing place of the displacement sensor and the detection point thereof are not limited to these. The invention may include any constitution that an element capable of detecting the relative displacement between the shaft and the bearing cup is disposed on the bearing-cup side, the displacement occurring when the shaft is deflected due to the damage produced on the rolling contact surface of the shaft. Specifically, a constitution may be made such that the displacement sensor takes measurement on a distance from the thrust washer inclined toward the bottom of the bearing cup when the shaft is deflected, as shown in FIG. 5(b), or measurement on an axial displacement of the shaft, thereby detecting the above relative displacement. While the foregoing description illustrates the case where the displacement sensor is disposed in correspondence to the aforesaid range of maximum load, the displacement sensor may be disposed on a line extended in parallel to the rotational direction of the spider joint and passing through the shaft center, or in proximity of the line. An alternative constitution may also be made wherein the displacement sensor is disposed in correspondence to a range of minimum load, which is on the opposite side from the range of maximum load or 180 deg. away therefrom with respect to the rotational direction of the spider joint.

While the description of Embodiment 1 illustrates the constitution employing the eddy-current displacement sensor, the invention does not limit the type of the sensor or the number of employed sensors so long as the above displacement can be detected by the sensor. Specific examples of the other usable displacement sensors include capacitance type sensors, photo-sensors, ultrasonic sensors, contact-type sensors and the like. However, the eddy-current sensor is more preferred because this sensor has a more compact structure than the other sensors, thus offering easy mounting. Furthermore, the eddy-current sensor is capable of correctly detecting the displacement even in a state where the sensor is dipped in the grease. Hence, the eddy-current sensor may be disposed in the bearing cup without closing an aperture of the sensor-mounting hole. In this respect as well, the eddy-current sensor is more preferred.

While the descriptions of Embodiments 2 and 3 illustrate the case where the ultrasonic sensor is disposed in the hole as the grease passage, the invention is not limited to this. An alternative constitution, for example, may be made such that a mounting space, such as a hole or recess, to mount the sensor is formed in the shafts of the cross shaft. However, the constitution wherein the ultrasonic sensor is disposed in the grease-passage hole formed in the shaft is more preferred in that the hole is advantageously utilized as the above mounting space, providing easy and low-cost mounting of the sensor.

While the description of Embodiment 3 illustrates the constitution wherein the ultrasonic sensor is fixed in the bearing cup at place spaced away from the inside wall of the hole, the invention is not limited to this. For instance, an alternative constitution may be made such that the ultrasonic sensor is fixed to place in the bearing cup by means of urging means such as a spring for urging the sensor toward the inside wall thereby to hold the distal end of the ultrasonic sensor in close contact against the inside wall at all times. Similarly to the constitution of Embodiment 2, this constitution prevents the formation of the interface between the substances having different densities on the propagation path of the ultrasonic wave. Accordingly, this constitution assuredly prevents the following problem. In Embodiment 3 adapted to locate the damaged point as shifting the ultrasonic scanning point according to the pivotal motion of the bearing cup, the sensor is decreased in the accuracy of locating the damaged point due to the existence of the above interface. What is more, this constitution permits the sensor to use the transverse ultrasonic wave.

What is claimed is:

1. A shaft coupling monitoring apparatus for monitoring a spider joint using outer peripheries of four shafts of a cross shaft as rolling contact surfaces for rolling motion of rolling elements,
    wherein each of the four shafts contain therein a sensor for detecting any damage on the rolling contact surface thereof, the sensor being located at a distal end of the shaft from the cross shaft, and the sensor being disposed in opposing relation with the rolling contact surface at said distal end.

2. A shaft coupling monitoring apparatus according to claim 1, wherein a bearing cup is pivotally mounted on each of the four shafts such that the bearing cup moves relative to a center of the shaft during rotational operation of the spider joint, and
    wherein a displacement sensor for detecting a relative displacement between the shaft and the bearing cup is used as said sensor and disposed inside the shaft and is fixed at the bearing cup, the displacement sensor being configured to pivot with the bearing cup as the bearing cup moves relative to the shaft.

3. A shaft coupling monitoring apparatus according to claim 2, wherein the displacement sensor is disposed on a line extending in parallel to a rotational direction of the spider joint and passing through the center of the shaft.

4. A shaft coupling monitoring apparatus according to claim 1, wherein an ultrasonic sensor capable of outputting an ultrasonic wave toward the rolling contact surface and receiving the ultrasonic wave reflected from the rolling contact surface is used as said sensor and disposed in the shaft.

5. A shaft coupling monitoring apparatus according to claim 4, wherein a bearing cup is pivotally mounted on each of the four shafts, and
    wherein the ultrasonic sensor is disposed in a mounting space provided in the shaft, as fixed to the bearing cup.

6. A shaft coupling monitoring apparatus according to claim 5, wherein the ultrasonic sensor outputs the ultrasonic wave toward the rolling contact surface, as held in close contact against a wall of the mounting space.

7. A shaft coupling monitoring apparatus according to claim 4, wherein the ultrasonic sensor is disposed in a hole formed as a grease passage in the shaft.

8. A shaft coupling monitoring apparatus according to claim 3, wherein the displacement sensor is disposed in a hole which is formed in the shaft in coaxial relation therewith, and detects the displacement by detecting a distance from an inside wall of the hole.

9. A shaft coupling monitoring apparatus according to claim 5, wherein the ultrasonic sensor is disposed in a hole formed as a grease passage in the shaft.

10. A shaft coupling monitoring apparatus according to claim 6, wherein the ultrasonic sensor is disposed in a hole formed as a grease passage in the shaft.

11. A shaft coupling monitoring apparatus for monitoring a spider joint using outer peripheries of four shafts of a cross shaft as rolling contact surfaces for rolling motion of rolling elements,
    wherein the shaft contains therein a sensor for detecting any damage on the rolling contact surface thereof,
    wherein a bearing cup is pivotally mounted on each of the four shafts,
    wherein a displacement sensor for detecting a relative displacement between the shaft and the bearing cup is used as said sensor and disposed at the bearing cup, and
    wherein the displacement sensor is disposed in a hole which is formed in the shaft in coaxial relation therewith, and detects the displacement by detecting a distance from an inside wall of the hole.

12. A shaft coupling monitoring apparatus according to claim 11, wherein the displacement sensor is disposed on a line extending in parallel to a rotational direction of the spider joint and passing through the center of the shaft.

13. A shaft coupling monitoring apparatus for monitoring a spider joint using outer peripheries of four shafts of a cross shaft as rolling contact surfaces for rolling motion of rolling elements,
    wherein the shaft contains therein a sensor for detecting any damage on the rolling contact surface thereof,
    wherein an ultrasonic sensor capable of outputting an ultrasonic wave toward the rolling contact surface and receiving the ultrasonic wave reflected from the rolling contact surface is used as said sensor and disposed in the shaft, and
    wherein the ultrasonic sensor outputs an ultrasonic outgoing wave toward the rolling contact surface as keeping the outgoing wave in phase with an ultrasonic reflective wave reflected from the rolling contact surface free from damage in order to receive an amplified ultrasonic wave reflected from the rolling contact surface.

14. A shaft coupling monitoring apparatus according to claim 13, wherein a bearing cup is pivotally mounted on each of the four shafts, and wherein the ultrasonic sensor is disposed in a mounting space provided in the shaft, as fixed to the bearing cup.

15. A shaft coupling monitoring apparatus according to claim 13, wherein the ultrasonic sensor is disposed in a hole formed as a grease passage in the shaft.

* * * * *